US012790590B2

(12) United States Patent
Smela et al.

(10) Patent No.: US 12,790,590 B2

(45) Date of Patent: *Nov. 10, 2026

(54) METHODS AND COMPOSITIONS FOR PRODUCING GRANULOSA-LIKE CELLS

(71) Applicant: President and Fellows of Harvard College, Cambridge, MA (US)

(72) Inventors: Merrick Pierson Smela, Cambridge, MA (US); Christian Kramme, Cambridge, MA (US); Pranam Chatterjee, Cambridge, MA (US); George M. Church, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/361,182

(22) Filed: Oct. 17, 2025

(65) Prior Publication Data

US 2026/0049287 A1 Feb. 19, 2026

Related U.S. Application Data

(63) Continuation of application No. 18/852,012, filed as application No. PCT/US2023/065140 on Mar. 30, 2023.

(60) Provisional application No. 63/444,108, filed on Feb. 8, 2023, provisional application No. 63/326,640, filed on Apr. 1, 2022.

(51) Int. Cl.

*C12N 5/071* (2010.01)
*C07K 14/47* (2006.01)
*C12N 5/074* (2010.01)

(52) U.S. Cl.

CPC ........ *C12N 5/0682* (2013.01); *C07K 14/4702* (2013.01); *C12N 5/0696* (2013.01); *C12N 2506/45* (2013.01); *C12N 2510/00* (2013.01); *C12N 2533/52* (2013.01)

(58) Field of Classification Search

CPC .............. C12N 5/0682; C12N 2506/45; C12N 2501/60

See application file for complete search history.

(56) References Cited

U.S. PATENT DOCUMENTS

| | | | |
|---|---|---|---|
| 11,136,555 B2 | 10/2021 | Ko | |
| 11,788,131 B2 * | 10/2023 | Ng | C12Q 1/34 435/6.11 |
| 2012/0107284 A1 | 5/2012 | Kozlova | |
| 2012/0207744 A1 | 8/2012 | Mendlein et al. | |
| 2016/0010056 A1 | 1/2016 | Nakaki et al. | |
| 2016/0237402 A1 | 8/2016 | Tilly et al. | |
| 2017/0087192 A1 | 3/2017 | Tilly et al. | |
| 2018/0072988 A1 | 3/2018 | Sun et al. | |
| 2018/0289748 A9 | 10/2018 | Tilly et al. | |
| 2020/0063105 A1 | 2/2020 | Ng et al. | |
| 2021/0054448 A1 | 2/2021 | Ng et al. | |
| 2025/0197807 A1 | 6/2025 | Smela et al. | |
| 2025/0207090 A1 | 6/2025 | Kramme et al. | |
| 2025/0207091 A1 | 6/2025 | Kramme et al. | |
| 2026/0035669 A1 | 2/2026 | Smela et al. | |

FOREIGN PATENT DOCUMENTS

| | | |
|---|---|---|
| CN | 102533778 A | 7/2012 |
| WO | WO 2017/079673 A1 | 5/2017 |
| WO | WO 2018/088240 A1 | 5/2018 |
| WO | WO 2021/034987 A1 | 2/2021 |
| WO | WO 2021/049613 A1 | 3/2021 |

OTHER PUBLICATIONS

LaVoie (MolReprodDev.2017;84:788-801.).*

Park (Mol Endocrinol, Apr. 2010, 24(4):846-858).*

Ford (Biology of Reproduction, 2022, 106(3), 503-514).*

[No Author Listed], Uniprot Accession No. 043680, Transcription factor 21. *Homo sapiens* (Human). Last updated Aug. 14, 2001. https://www.uniprot.org/uniprotkb/O43680/entry. 7 pages.

[No Author Listed], Uniprot Accession No. P43694, Transcription factor GATA-4. *Homo sapiens* (Human). Last updated Nov. 25, 2008. https://www.uniprot.org/uniprotkb/P43694/entry. 19 pages.

[No Author Listed], Uniprot Accession No. P56178, Homeobox protein DLX-5. *Homo sapiens* (Human). Last updated Jan. 11, 2001. https://www.uniprot.org/uniprotkb/P56178/entry. 9 pages.

[No Author Listed], Uniprot Accession No. Q01196, Runt-related transcription factor 1. *Homo sapiens* (Human). Last updated Nov. 25, 2008.https://www.uniprot.org/uniprotkb/Q01196/entry. 19 pages.

[No Author Listed], Uniprot Accession No. Q03014, Hematopoietically-expressed homeobox protein HHEX. *Homo sapiens* (Human). Last updated Jun. 1, 1994. https://www.uniprot.org/uniprotkb/Q03014/entry. 9 pages.

[No Author Listed], Uniprot Accession No. Q13285, Steroidogenic factor 1. *Homo sapiens* (Human). Last updated Jan. 1, 1998.https://www.uniprot.org/uniprotkb/Q13285/entry. 11 pages.

[No Author Listed], Uniprot Accession No. Q13950, Runt-related transcription factor 2. *Homo sapiens* (Human). Last updated Nov. 2, 2001. https://www.uniprot.org/uniprotkb/Q13950/entry. 13 pages.

[No Author Listed], Uniprot Accession No. Q68G74, LIM/homeobox protein Lhx8. *Homo sapiens* (Human). Last updated May 18, 2010. https://www.uniprot.org/uniprotkb/Q68G74/entry. 9 pages.

[No Author Listed], Uniprot Accession No. Q6IUP1, Spermatogenesis- and oogenesis-specific basic helix-loop-helix-containing protein 1. (SOHLH1_Mouse). Last updated Jul. 5, 2004. https://www.uniprot.org/uniprotkb/Q6IUP1/entry. 6 pages.

(Continued)

*Primary Examiner* — Valarie E Bertoglio

(74) *Attorney, Agent, or Firm* — Wolf, Greenfield & Sacks, P.C.

(57) ABSTRACT

Provided herein are methods and compositions for differentiating induced pluripotent stem cells into granulosa-like cells by overexpressing transcription factors such as NR5A1 and a RUNX family protein (e.g., RUNX1 and/or RUNX2).

25 Claims, 12 Drawing Sheets

Specification includes a Sequence Listing.

(56) References Cited

OTHER PUBLICATIONS

[No Author Listed], Uniprot Accession No. Q6QHK4, Factor in the germline alpha (FIGLA). *Homo sapiens* (Human). Last updated May 18, 2010. https://www.uniprot.org/uniprotkb/Q6QHK4/entry. 8 pages.
[No Author Listed], Uniprot Accession No. Q8N9W6, Protein boule-like (BOLL). *Homo sapiens* (Human). Last updated Mar. 1, 2004. https://www.uniprot.org/uniprotkb/Q8N9W6/entry. 13 pages.
[No Author Listed], Uniprot Accession No. Q92904, Deleted in azoospermia-like (DAZL). *Homo sapiens* (Human). Last updated Feb. 1, 1997. https://www.uniprot.org/uniprotkb/Q92904/entry. 8 pages.
[No Author Listed], Uniprot Accession No. Q9NQIO, Probable ATP-dependent RNA helicase DDX4. *Homo sapiens* (Human). Last updated Jan. 23, 2002. https://www.uniprot.org/uniprotkb/Q9NQI0/entry. 11 pages.
[No Author Listed], Uniprot Accession No. Q9Y2X9, Zinc finger protein 281. *Homo sapiens* (Human). Last updated Nov. 1, 1999. https://www.uniprot.org/uniprotkb/Q9Y2X9/entry. 10 pages.
Albertini et al., Cellular basis for paracrine regulation of ovarian follicle development. Reproduction. May 2001;121(5):647-53. doi: 10.1530/rep.0.1210647.
Cocquet et al., Evolution and expression of FOXL2. J Med Genet. Dec. 2002;39(12):916-21. doi: 10.1136/jmg.39.12.916.
Fossett et al., Optimising human mesenchymal stem cell numbers for clinical application: a literature review. Stem Cells Int. 2012; 2012:465259. doi: 10.1155/2012/465259. Epub Jan. 31, 2012.
Garcia-Alonso et al., Single-cell roadmap of human gonadal development. Nature. Jul. 2022;607(7919):540-547. doi: 10.1038/s41586-022-04918-4. Epub Jul. 6, 2022. Suppl Info, 27 pages.
Gill et al., Licensing of gametogenesis, dependent on RNA binding protein DAZL, as a gateway to sexual differentiation of fetal germ cells. Proc Natl Acad Sci U S A. May 3, 2011;108(18):7443-8. doi: 10.1073/pnas.1104501108. Epub Apr. 19, 2011.
Gonen et al., In vitro cellular reprogramming to model gonad development and its disorders. Sci Adv. Jan. 4, 2023;9(1):eabn9793. doi: 10.1126/sciadv.abn9793. Epub Jan. 4, 2023.
Gustin et al., WNT/β-catenin and p27/FOXL2 differentially regulate supporting cell proliferation in the developing ovary. Dev Biol. Apr. 15, 2016;412(2):250-60. doi: 10.1016/j.ydbio.2016.02.024. Epub Mar. 3, 2016.
Havelock et al., Ovarian granulosa cell lines. Mol Cell Endocrinol. Dec. 30, 2004;228(1-2):67-78. doi: 10.1016/j.mce.2004.04.018.
Hayashi et al., Reconstitution of the mouse germ cell specification pathway in culture by pluripotent stem cells. Cell. Aug. 19, 2011;146(4):519-32. doi: 10.1016/j.cell.2011.06.052. Epub Aug. 4, 2011.
Hong et al., Germ Cell Derivation from Pluripotent Stem Cells for Understanding In Vitro Gametogenesis. Cells. Jul. 26, 2021;10(8):1889. doi: 10.3390/cells10081889.
Høyer et al., Stem cell factor and c-Kit in human primordial germ cells and fetal ovaries. Mol Cell Endocrinol. Apr. 29, 2005;234(1-2):1-10. doi: 10.1016/j.mce.2004.09.012.
Hu et al., Licensing of primordial germ cells for gametogenesis depends on genital ridge signaling. PLoS Genet. Mar. 4, 2015;11(3):e1005019. doi: 10.1371/journal.pgen.1005019.
Huang et al., Tankyrase inhibition stabilizes axin and antagonizes Wnt signalling. Nature. Oct. 1, 2009;461(7264):614-20. doi: 10.1038/nature08356. Epub Sep. 16, 2009.
Hwang et al., Reconstitution of prospermatogonial specification in vitro from human induced pluripotent stem cells. Nat Commun. Nov. 9, 2020;11(1):5656. doi: 10.1038/s41467-020-19350-3.
Irie et al., Efficient Induction and Isolation of Human Primordial Germ Cell-Like Cells from Competent Human Pluripotent Stem Cells. Methods Mol Biol. 2017;1463:217-226. doi: 10.1007/978-1-4939-4017-2_16.
Irie et al., SOX17 is a critical specifier of human primordial germ cell fate. Cell. Jan. 15, 2015;160(1-2):253-68. doi: 10.1016/j.cell.2014.12.013. Epub Dec. 24, 2014.
Jadhav et al., Steroidogenic factor-1 (SF-1)-driven differentiation of murine embryonic stem (ES) cells into a gonadal lineage. Endocrinology. Jul. 2011;152(7):2870-82. doi: 10.1210/en.2011-0219. Epub May 24, 2011.
Kee et al., Bone morphogenetic proteins induce germ cell differentiation from human embryonic stem cells. Stem Cells Dev. Dec. 2006;15(6):831-7. doi: 10.1089/scd.2006.15.831.
Kobayashi et al., Expanding homogeneous culture of human primordial germ cell-like cells maintaining germline features without serum or feeder layers. Stem Cell Reports. Mar. 8, 2022;17(3):507-521. doi: 10.1016/j.stemcr.2022.01.012. Epub Feb. 10, 2022.
Kramme et al., An integrated pipeline for mammalian genetic screening. Cell Rep Methods. Sep. 27, 2021;1(6):100082. doi: 10.1016/j.crmeth.2021.100082.
Lan et al., Differentiation of human embryonic stem cells into functional ovarian granulosa-like cells. J Clin Endocrinol Metab. Sep. 2013;98(9):3713-23. doi: 10.1210/jc.2012-4302. Epub Jul. 24, 2013.
Lawson et al., Bmp4 is required for the generation of primordial germ cells in the mouse embryo. Genes Dev. Feb. 15, 1999;13(4):424-36. doi: 10.1101/gad.13.4.424.
Lecluze et al., Dynamics of the transcriptional landscape during human fetal testis and ovary development. Hum Reprod. May 1, 2020;35(5):1099-1119. doi: 10.1093/humrep/deaa041.
Li et al., Directing differentiation of human induced pluripotent stem cells toward androgen-producing Leydig cells rather than adrenal cells. Proc Natl Acad Sci U S A. Nov. 12, 2019;116(46):23274-23283. doi: 10.1073/pnas.1908207116. Epub Oct. 7, 2019.
Liang et al., Induction of Sertoli-like cells from human fibroblasts by NR5A1 and GATA4. Elife. Nov. 11, 2019;8:e48767. doi: 10.7554/eLife.48767.
Lipskind et al., An Embryonic and Induced Pluripotent Stem Cell Model for Ovarian Granulosa Cell Development and Steroidogenesis. Reprod Sci. May 2018;25(5):712-726. doi: 10.1177/1933719117725814. Epub Aug. 31, 2017.
Mall et al., A novel xeno-organoid approach: exploring the crosstalk between human iPSC-derived PGC-like and rat testicular cells. Mol Hum Reprod. Dec. 10, 2020;26(12):879-893. doi: 10.1093/molehr/gaaa067.
Manuylov et al., Ovarian development in mice requires the GATA4-FOG2 transcription complex. Development. Nov. 2008;135(22):3731-43. doi: 10.1242/dev.024653. Epub Oct. 16, 2008.
Mitsunaga et al., Relevance of iPSC-derived human PGC-like cells at the surface of embryoid bodies to prechemotaxis migrating PGCs. Proc Natl Acad Sci U S A. Nov. 14, 2017;114(46):E9913-E9922. doi: 10.1073/pnas.1707779114. Epub Oct. 30, 2017.
Mizuta et al., Ex vivo reconstitution of fetal oocyte development in humans and cynomolgus monkeys. EMBO J. Sep. 15, 2022;41(18):e110815. doi: 10.15252/embj.2022110815. Epub Aug. 1, 2022.
Murase et al., Long-term expansion with germline potential of human primordial germ cell-like cells in vitro. Embo J. Nov. 2, 2020;39(21):e104929. doi: 10.15252/embj.2020104929. Epub Sep. 20, 2020.
Ng et al., A comprehensive library of human transcription factors for cell fate engineering. Nat Biotechnol. Apr. 2021;39(4):510-519. doi: 10.1038/s41587-020-0742-6. Epub Nov. 30, 2020. Author Manuscript, 37 pages.
Nicol et al., Genome-wide identification of FOXL2 binding and characterization of FOXL2 feminizing action in the fetal gonads. Hum Mol Genet. Dec. 15, 2018;27(24):4273-4287. doi: 10.1093/hmg/ddy312.
Nicol et al., RUNX1 maintains the identity of the fetal ovary through an interplay with FOXL2. Nat Commun. Nov. 11, 2019;10(1):5116. doi: 10.1038/s41467-019-13060-1.
Nishi et al., Establishment and characterization of a steroidogenic human granulosa-like tumor cell line, KGN, that expresses functional follicle-stimulating hormone receptor. Endocrinology. Jan. 2001;142(1):437-45. doi: 10.1210/endo.142.1.7862.

(56) References Cited

OTHER PUBLICATIONS

Niu et al., Two distinct pathways of pregranulosa cell differentiation support follicle formation in the mouse ovary. Proc Natl Acad Sci U S A. Aug. 18, 2020;117(33):20015-20026. doi: 10.1073/pnas.2005570117. Epub Aug. 5, 2020.
Oktay et al., Ontogeny of follicle-stimulating hormone receptor gene expression in isolated human ovarian follicles. J Clin Endocrinol Metab. Nov. 1997;82(11):3748-51. doi: 10.1210/jcem.82.11.4346.
Ottolenghi et al., Fox12 is required for commitment to ovary differentiation. Hum Mol Genet. Jul. 15, 2005;14(14):2053-62. doi: 10.1093/hmg/ddi210. Epub Jun. 8, 2005.
Peng et al., Growth differentiation factor 9:bone morphogenetic protein 15 heterodimers are potent regulators of ovarian functions. Proc Natl Acad Sci U S A. Feb. 19, 2013;110(8):E776-85. doi: 10.1073/pnas.1218020110. Epub Feb. 4, 2013.
Pierson Smela et al., Rapid human oogonia-like cell specification via transcription factor-directed differentiation. EMBO Rep. Feb. 2025;26(4):1114-1143. doi: 10.1038/s44319-025-00371-2. Epub Jan. 23, 2025.
Price et al., Toll-like receptor expression and function in the COV434 granulosa cell line. Am J Reprod Immunol. Sep. 2012;68(3):205-17. doi: 10.1111/j.1600-0897.2011.01103.x. Epub Jan. 11, 2012.
Rodrigues et al., Germ-Somatic Cell Interactions Are Involved in Establishing the Follicle Reserve in Mammals. Front Cell Dev Biol. Jun. 14, 2021;9:674137. doi: 10.3389/fcell.2021.674137.
Sasaki et al., Robust In Vitro Induction of Human Germ Cell Fate from Pluripotent Stem Cells. Cell Stem Cell. Aug. 6, 2015;17(2):178-94. doi: 10.1016/j.stem.2015.06.014. Epub Jul. 16, 2015.
Shi et al., Induced pluripotent stem cell technology: a decade of progress. Nat Rev Drug Discov. Feb. 2017;16(2):115-130. doi: 10.1038/nrd.2016.245. Epub Dec. 16, 2016. Author Manuscript, 39 pages.
Sosa et al., Differentiation of primate primordial germ cell-like cells following transplantation into the adult gonadal niche. Nat Commun. Dec. 17, 2018;9(1):5339. doi: 10.1038/s41467-018-07740-7.
Stévant et al., Dissecting Cell Lineage Specification and Sex Fate Determination in Gonadal Somatic Cells Using Single-Cell Transcriptomics. Cell Rep. Mar. 19, 2019;26(12):3272-3283.e3. doi: 10.1016/j.celrep.2019.02.069. Suppl Info, 3 pages.
Su et al., Synergistic roles of BMP15 and GDF9 in the development and function of the oocyte-cumulus cell complex in mice: genetic evidence for an oocyte-granulosa cell regulatory loop. Dev Biol. Dec. 1, 2004;276(1):64-73. doi: 10.1016/j.ydbio.2004.08.020.
Sybirna et al., A critical role of PRDM14 in human primordial germ cell fate revealed by inducible degrons. Nat Commun. Mar. 9, 2020;11(1):1282. doi: 10.1038/s41467-020-15042-0.
Takahashi et al., Induction of pluripotent stem cells from mouse embryonic and adult fibroblast cultures by defined factors. Cell. Aug. 25, 2006;126(4):663-76. doi: 10.1016/j.cell.2006.07.024. Epub Aug. 10, 2006.
Tang et al., Specification and epigenetic programming of the human germ line. Nat Rev Genet. Oct. 2016;17(10):585-600. doi: 10.1038/nrg.2016.88. Epub Aug. 30, 2016.
Vijayakumar et al., Monolayer platform to generate and purify primordial germ-like cells in vitro provides insights into human germline specification. Nat Commun. Sep. 14, 2023;14(1):5690. doi: 10.1038/s41467-023-41302-w.
Voronina et al., Ovarian granulosa cell survival and proliferation requires the gonad-selective TFIID subunit TAF4b. Dev Biol. Mar. 15, 2007;303(2):715-26. doi: 10.1016/j.ydbio.2006.12.011. Epub Dec. 9, 2006.
Welsh et al., Forskolin and phosphodiesterase inhibitors stimulate rat granulosa cell differentiation. Mol Cell Endocrinol. Aug. 1984;37(1):51-60. doi: 10.1016/0303-7207(84)90127-8.
Woods et al., Embryonic stem cell-derived granulosa cells participate in ovarian follicle formation in vitro and in vivo. Reprod Sci. May 2013;20(5):524-35. doi: 10.1177/1933719113483017. Epub Mar. 27, 2013.
Yamashiro et al., Generation of human oogonia from induced pluripotent stem cells in vitro. Science. Oct. 19, 2018;362(6412):356-360. doi: 10.1126/science.aat1674. Epub Sep. 20, 2018.
Yan et al., DAZL regulates proliferation of human primordial germ cells by direct binding to precursor miRNAs and enhances DICER processing activity. Nucleic Acids Res. Oct. 28, 2022;50(19):11255-11272. doi: 10.1093/nar/gkac856.
Yazawa et al., Transcriptional Regulation of Ovarian Steroidogenic Genes: Recent Findings Obtained from Stem Cell-Derived Steroidogenic Cells. Biomed Res Int. Apr. 1, 2019;2019:8973076. doi: 10.1155/2019/8973076.
Yoshino et al., Generation of ovarian follicles from mouse pluripotent stem cells. Science. Jul. 16, 2021;373(6552):eabe0237. doi: 10.1126/science.abe0237.
Zhang et al., Characterization of an immortalized human granulosa cell line (COV434). Mol Hum Reprod. Feb. 2000;6(2):146-53. doi: 10.1093/molehr/6.2.146.
Zhang et al., Transcriptome Landscape of Human Folliculogenesis Reveals Oocyte and Granulosa Cell Interactions. Mol Cell. Dec. 20, 2018;72(6):1021-1034.e4. doi: 10.1016/j.molcel.2018.10.029. Epub Nov. 21, 2018. Suppl Info, 4 pages.
Hamazaki et al., Reconstitution of the oocyte transcriptional network with transcription factors. Nature. Jan. 2021;589(7841):264-269. doi: 10.1038/s41586-020-3027-9. Epub Dec. 16, 2020.
Ishida et al., Differentiation of Human Induced Pluripotent Stem Cells Into Testosterone-Producing Leydig-like Cells. Endocrinology. Dec. 1, 2021;162(12):bqab202. doi: 10.1210/endocr/bqab202.
Kramme et al., Efficient Human Germ Cell Specification from Stem Cells via Combinatorial Expression of Transcription Factors. bioRxiv. Jul. 12, 2022. doi: 10.1101/2022.07.11.499564. 20 pages.
Nakaki et al., Induction of mouse germ-cell fate by transcription factors in vitro. Nature. Sep. 12, 2013;501(7466):222-6. doi: 10.1038/nature12417. Epub Aug. 4, 2013.
Pierson Smela et al., Directed differentiation of human iPSCs to functional ovarian granulosa-like cells via transcription factor overexpression. Elife. Feb. 21, 2023;12:e83291. doi: 10.7554/eLife.83291. Erratum in: Elife. Mar. 22, 2023;12:e87987. doi: 10.7554/eLife.87987.
Ran et al., RUNX1a enhances hematopoietic lineage commitment from human embryonic stem cells and inducible pluripotent stem cells. Blood. Apr. 11, 2013;121(15):2882-90. doi: 10.1182/blood-2012-08-451641. Epub Jan. 31, 2013.
Saitou et al., Mechanisms of human germ cell development. Nat Rev Mol Cell Biol. Feb. 2026;27(2):153-171. doi: 10.1038/s41580-025-00893-6. Epub Sep. 16, 2025.
Yamauchi et al., Overexpression of Nuclear Receptor 5A1 Induces and Maintains an Intermediate State of Conversion between Primed and Naive Pluripotency. Stem Cell Reports. Mar. 10, 2020;14(3):506-519. doi: 10.1016/j.stemcr.2020.01.012. Epub Feb. 20, 2020.
Yu et al., Human pluripotent stem cell-derived DDX4 and KRT-8 positive cells participate in ovarian follicle-like structure formation. iScience. Dec. 29, 2020;24(1):102003. doi: 10.1016/j.isci.2020.102003.

* cited by examiner

| NR5A1 | RUNX1 | RUNX2 | TCF21 | GATA4 | NR2F2 | KLF2 | WT1 | FOXL2 | Estradiol pg/µL | All markers % | AMHR2 % | CD82 % | FOXL2 % | EPCAM % |
|---|---|---|---|---|---|---|---|---|---|---|---|---|---|---|
| 0 | 0 | 0 | 0 | 0 | 0 | 0 | 0 | 0 | 23 | 0.8 | 3.5 | 9.6 | 1.3 | 90.1 |
| 1 | 0 | 0 | 0 | 0 | 0 | 0 | 0 | 0 | 2703 | 0.6 | 2.6 | 30.9 | 2.0 | 56.5 |
| 0 | 1 | 0 | 0 | 0 | 0 | 0 | 0 | 0 | 10 | 4.3 | 7.8 | 40.5 | 10.3 | 13.2 |
| 0 | 0 | 1 | 0 | 0 | 0 | 0 | 0 | 0 | 11 | 4.2 | 6.5 | 63.9 | 8.8 | 15.3 |
| 0 | 0 | 0 | 1 | 0 | 0 | 0 | 0 | 0 | 98 | 0.5 | 1.8 | 21.7 | 1.4 | 51.1 |
| 0 | 0 | 0 | 0 | 1 | 0 | 0 | 0 | 0 | 265 | 0.3 | 1.5 | 13.6 | 0.7 | 35.9 |
| 0 | 0 | 0 | 0 | 0 | 1 | 0 | 0 | 0 | 30 | 1.7 | 4.6 | 9.7 | 3.5 | 6.8 |
| 0 | 0 | 0 | 0 | 0 | 0 | 1 | 0 | 0 | 190 | 1.0 | 3.3 | 9.5 | 2.3 | 35.5 |
| 0 | 0 | 0 | 0 | 0 | 0 | 0 | 1 | 0 | 55 | 1.2 | 2.9 | 31.9 | 2.0 | 16.0 |
| 0 | 0 | 0 | 0 | 0 | 0 | 0 | 0 | 1 | 35 | 1.7 | 4.8 | 31.4 | 4.2 | 13.7 |
| 1 | 1 | 0 | 0 | 0 | 0 | 0 | 0 | 0 | 71 | 4.3 | 12.1 | 31.2 | 10.1 | 22.6 |
| 1 | 0 | 1 | 0 | 0 | 0 | 0 | 0 | 0 | 170 | 7.6 | 48.4 | 57.6 | 14.3 | 13.9 |
| 1 | 0 | 0 | 1 | 0 | 0 | 0 | 0 | 0 | 524 | 0.5 | 2.5 | 26.4 | 1.2 | 53.1 |
| 1 | 0 | 0 | 0 | 1 | 0 | 0 | 0 | 0 | 504 | 0.3 | 3.6 | 18.4 | 0.7 | 42.8 |
| 1 | 0 | 0 | 0 | 0 | 1 | 0 | 0 | 0 | 57 | 0.9 | 3.7 | 8.9 | 2.1 | 10.6 |
| 1 | 0 | 0 | 0 | 0 | 0 | 1 | 0 | 0 | 177 | 0.4 | 3.5 | 12.3 | 1.2 | 27.5 |
| 1 | 0 | 0 | 0 | 0 | 0 | 0 | 1 | 0 | 95 | 0.8 | 3.1 | 25.1 | 1.3 | [illegible] |
| 1 | 0 | 0 | 0 | 0 | 0 | 0 | 0 | 1 | 42 | 0.7 | 4.0 | 17.5 | 2.0 | 13.7 |
| 1 | 1 | 1 | 0 | 0 | 0 | 0 | 0 | 0 | 289 | 3.7 | 9.1 | 27.4 | 10.4 | 34.1 |
| 1 | 1 | 0 | 1 | 0 | 0 | 0 | 0 | 0 | 737 | 2.0 | 6.2 | 33.0 | 5.3 | 44.1 |
| 1 | 1 | 0 | 0 | 1 | 0 | 0 | 0 | 0 | 868 | 2.0 | 6.0 | 29.9 | 4.1 | 37.3 |
| 1 | 1 | 0 | 0 | 0 | 1 | 0 | 0 | 0 | 405 | 2.2 | 7.5 | 20.7 | 5.2 | [illegible] |
| 1 | 1 | 0 | 0 | 0 | 0 | 1 | 0 | 0 | 165 | 0.6 | 3.9 | 8.5 | 1.7 | 23.6 |
| 1 | 1 | 0 | 0 | 0 | 0 | 0 | 1 | 0 | 115 | 2.2 | 5.9 | 22.9 | 4.1 | 15.7 |
| 1 | 1 | 0 | 0 | 0 | 0 | 0 | 0 | 1 | 123 | 1.3 | 3.6 | 26.9 | 3.4 | 9.9 |
| 1 | 0 | 1 | 1 | 0 | 0 | 0 | 0 | 0 | 347 | 3.3 | 6.5 | 33.0 | 7.1 | 35.7 |
| 1 | 0 | 1 | 0 | 1 | 0 | 0 | 0 | 0 | 657 | 1.6 | 5.9 | 32.8 | 3.3 | 39.6 |
| 1 | 0 | 1 | 0 | 0 | 1 | 0 | 0 | 0 | 194 | 2.4 | 6.3 | 18.6 | 5.0 | 17.2 |
| 1 | 0 | 1 | 0 | 0 | 0 | 1 | 0 | 0 | 1138 | 0.9 | 4.8 | 9.7 | 2.3 | 31.3 |
| 1 | 0 | 1 | 0 | 0 | 0 | 0 | 1 | 0 | 165 | 1.5 | 3.7 | 22.3 | 2.6 | 18.1 |
| 1 | 0 | 1 | 0 | 0 | 0 | 0 | 0 | 1 | 114 | 1.4 | 4.1 | 24.6 | 3.6 | 9.7 |
| 1 | 0 | 0 | 1 | 1 | 0 | 0 | 0 | 0 | 237 | 0.7 | 3.6 | 22.5 | 1.4 | 35.3 |
| 1 | 0 | 0 | 1 | 0 | 1 | 0 | 0 | 0 | 107 | 1.2 | 4.3 | 14.8 | 2.4 | 16.7 |
| 1 | 0 | 0 | 1 | 0 | 0 | 1 | 0 | 0 | 296 | 0.9 | 7.4 | 15.2 | 2.2 | 34.2 |
| 1 | 0 | 0 | 1 | 0 | 0 | 0 | 1 | 0 | 64 | 2.0 | [illegible] | 24.3 | 4.2 | 20.4 |
| 1 | 0 | 0 | 1 | 0 | 0 | 0 | 0 | 1 | 76 | 1.0 | 3.8 | 20.9 | 2.9 | 10.8 |
| 1 | 0 | 0 | 0 | 1 | 1 | 0 | 0 | 0 | 191 | 1.1 | 2.8 | 13.8 | 2.2 | 21.1 |
| 1 | 0 | 0 | 0 | 1 | 0 | 1 | 0 | 0 | 2132 | 0.5 | 1.9 | 8.2 | 1.3 | 27.3 |
| 1 | 0 | 0 | 0 | 1 | 0 | 0 | 1 | 0 | 291 | 0.6 | 2.3 | 26.0 | 1.1 | 32.1 |
| 1 | 0 | 0 | 0 | 1 | 0 | 0 | 0 | 1 | 256 | 1.0 | 8.3 | 25.8 | 2.1 | 18.6 |
| 1 | 0 | 0 | 0 | 0 | 1 | 1 | 0 | 0 | 878 | 0.6 | 4.2 | 12.7 | 1.6 | 23.8 |
| 1 | 0 | 0 | 0 | 0 | 1 | 0 | 1 | 0 | 146 | 1.0 | 2.9 | 20.8 | 1.9 | 40.2 |
| 1 | 0 | 0 | 0 | 0 | 1 | 0 | 0 | 1 | 150 | 1.4 | 3.9 | 24.4 | 2.9 | 9.8 |
| 1 | 0 | 0 | 0 | 0 | 0 | 1 | 1 | 0 | 344 | 0.3 | 2.2 | 13.5 | 0.7 | 28.5 |
| 1 | 0 | 0 | 0 | 0 | 0 | 1 | 0 | 1 | 361 | 0.6 | 2.6 | 17.8 | 1.4 | 23.9 |
| 1 | 0 | 0 | 0 | 0 | 0 | 0 | 1 | 1 | 79 | 1.0 | 3.6 | 18.1 | 2.2 | 9.6 |
| 1 | 1 | 1 | 1 | 1 | 0 | 0 | 1 | 1 | 457 | 1.9 | 7.4 | 39.7 | 3.8 | 25.7 |
| 1 | 1 | 1 | 1 | 1 | 1 | 1 | 1 | 1 | 1973 | 0.9 | 3.6 | 28.4 | 1.9 | 37.8 |

FIG. 2

| Gonad / Granulosa | Gonad_wk7 | primary_GC | primordial_GC | FOXL2 tdT+ | COV434 | iPSC |
|---|---|---|---|---|---|---|
| *ALDH1A2* | 6.6 | 1.3 | 1.7 | 5.1 | 0.3 | 0.2 |
| *AMHR2* | 6.3 | 2.5 | 2.5 | 4.1 | 0.1 | 0.1 |
| *CD82* | 1.9 | 2.8 | 4.9 | 4.5 | 1.7 | 3.2 |
| *CDH2* | 7.1 | 2.6 | 0.9 | 6.5 | 1.9 | 5.5 |
| *COL1A1* | 9.5 | 1.2 | 0.9 | 8.9 | 1.4 | 4.9 |
| *CXCL12* | 8.0 | 0.4 | 0.4 | 5.8 | 0.2 | 5.9 |
| *FOXL2* | 0.9 | 3.3 | 4.2 | 3.7 | 0.0 | 1.1 |
| *FSHR* | 1.4 | 0.6 | 0.4 | 0.4 | 0.0 | 0.0 |
| *IGF2* | 9.9 | 0.8 | 1.0 | 11.2 | 5.2 | 2.1 |
| *IGFBP7* | 5.3 | 6.3 | 2.3 | 8.8 | 9.5 | 1.2 |
| *KRT19* | 3.7 | 1.4 | 2.6 | 7.1 | 0.0 | 6.7 |
| *LHX9* | 7.3 | 0.0 | 0.1 | 0.3 | 0.4 | 0.0 |
| *MYRF* | 7.5 | 0.9 | 1.1 | 3.4 | 1.0 | 1.4 |
| *NR2F2* | 9.0 | 1.9 | 1.2 | 6.5 | 7.5 | 0.2 |
| *NR5A1* | 5.5 | 0.7 | 0.0 | 11.3 | 0.1 | 1.6 |
| *RSPO1* | 4.8 | 0.0 | 0.0 | 0.8 | 0.1 | 0.1 |
| *STAR* | 7.0 | 3.7 | 4.0 | 7.8 | 0.1 | 1.6 |
| *TCF21* | 4.6 | 0.9 | 0.8 | 9.4 | 0.0 | 1.0 |
| *VIM* | 8.2 | 9.0 | 9.3 | 10.1 | 3.6 | 5.7 |
| *WNT4* | 4.1 | 0.0 | 0.0 | 2.4 | 0.3 | 0.3 |
| *WT1* | 8.6 | 2.2 | 2.3 | 0.3 | 7.9 | 0.0 |
| **Adrenal** | | | | | | |
| *NTRK2* | 5.9 | 0.7 | 0.8 | 0.8 | 2.7 | 0.1 |
| *OSR2* | 1.8 | 0.4 | 1.0 | 0.7 | 2.2 | 0.4 |
| **Pluripotent** | | | | | | |
| *SOX2* | 0.1 | 0.1 | 0.1 | 1.3 | 0.9 | 7.8 |
| *NANOG* | 2.9 | 0.4 | 0.1 | 0.6 | 0.1 | 8.2 |
| *POU5F1* | 0.5 | 0.24 | 0.1 | 4.2 | 0.6 | 11.1 |

FIG. 3

SEQUENCE LISTING

```
Sequence total quantity: 5
SEQ ID NO: 1            moltype = AA  length = 461
FEATURE                 Location/Qualifiers
source                  1..461
                        mol_type = protein
                        organism = synthetic construct
SEQUENCE: 1
MDYSYDEDLD ELCPVCGDKV SGYHYGLLTC ESCKGFFKRT VQNNKHYTCT ESQSCKIDKT  60
QRKRCPFCRF QKCLTVGMRL EAVRADRMRG GRNKFGPMYK RDRALKQQKK AQIRANGFKL  120
ETGPPMGVPP PPPPAPDYVL PPSLHGPEPK GLAAGPPAGP LGDFGAPALP MAVPGAHGPL  180
AGYLYPAFPG RAIKSEYPEP YASPPQPGLP YGYPEPFSGG PNVPELILQL LQLEPDEDQV  240
RARILGCLQE PTKSRPDQPA AFGLLCRMAD QTFISIVDWA RRCMVFKELE VADQMTLLQN  300
CWSELLVFDH IYRQVQHGKE GSILLVTGQE VELTTVATQA GSLLHSLVLR AQELVLQLLA  360
LQLDRQEFVC LKFIILFSLD LKFLNNHILV KDAQEKANAA LLDYTLCHYP HCGDKFQQLL  420
LCLVEVRALS MQAKEYLYHK HLGNEMPRNN LLIEMLQAKQ T                    461

SEQ ID NO: 2            moltype = AA  length = 453
FEATURE                 Location/Qualifiers
source                  1..453
                        mol_type = protein
                        organism = unidentified
SEQUENCE: 2
MRIPVDASTS RRFTPPSTAL SPGKMSEALP LGAPDAGAAL AGKLRSGDRS MVEVLADHPG  60
ELVRTDSPNF LCSVLPTHWR CNKTLPIAFK VVALGDVPDG TLVTVMAGND ENYSAELRNA  120
TAAMKNQVAR FNDLRFVGRS GRGKSFTLTI TVFTNPPQVA TYHRAIKITV DGPREPRRHR  180
QKLDDQTKPG SLSFSERLSE LEQLRRTAMR VSPHHPAPTP NPRASLNHST AFNPQPQSQM  240
QDTRQIQPSP PWSYDQSYQY LGSIASPSVH PATPISPGRA SGMTTLSAEL SSRLSTAPDL  300
TAFSDPRQFP ALPSISDPRM HYPGAFTYSP TPVTSGIGIG MSAMGSATRY HTYLPPPYPG  360
SSQAQGGPFQ ASSPSYHLYY GASAGSYQFS MVGGERSPPR ILPPCTNAST GSALLNPSLP  420
NQSDVVEAEG SHSNSPTNMA PSARLEEAVW RPY                              453

SEQ ID NO: 3            moltype = AA  length = 521
FEATURE                 Location/Qualifiers
source                  1..521
                        mol_type = protein
                        organism = synthetic construct
SEQUENCE: 3
```

-continued

```
MASNSLFSTV TPCQQNFFWD PSTSRRFSPP SSSLQPGKMS DVSPVVAAQQ QQQQQQQQQQ  60
QQQQQQQQQQ QEAAAAAAAA AAAAAAAAAV PRLRPPHDNR TMVEIIADHP AELVRTDSPN  120
FLCSVLPSHW RCNKTLPVAF KVVALGEVPD GTVVTVMAGN DENYSAELRN ASAVMKNQVA  180
RFNDLRFVGR SGRGKSFTLT ITVFTNPPQV ATYHRAIKVT VDGPREPRRH RQKLDDSKPS  240
LFSDRLSDLG RIPHPSMRVG VPPQNPRPSL NSAPSPFNPQ GQSQITDPRQ AQSSPPWSYD  300
QSYPSYLSQM TSPSIHSTTP LSSTRGTGLP AITDVPRRIS DDDTATSDFC LWPSTLSKKS  360
QAGASELGPF SDPRQFPSIS SLTESRFSNP RMHYPATFTY TPPVTSGMSL GMSATTHYHT  420
YLPPPYPGSS QSQSGPFQTS STPYLYYGTS SGSYQFPMVP GGDRSPSRML PPCTTTSNGS  480
TLLNPNLPNQ NDGVDADGSH SSSPTVLNSS GRMDESVWRP Y                     521

SEQ ID NO: 4            moltype = AA  length = 179
FEATURE                 Location/Qualifiers
source                  1..179
                        mol_type = protein
                        organism = synthetic construct
SEQUENCE: 4
MSTGSLSDVE DLQEVEMLEC DGLKMDSNKE FVTSNESTEE SSNCENGSPQ KGRGGLGKRR  60
KAPTKKSPLS GVSQEGKQVQ RNAANARERA RMRVLSKAFS RLKTTLPWVP PDTKLSKLDT  120
LRLASSYIAH LRQILANDKY ENGYIHPVNL TWPFMVAGKP ESDLKEVVTA SRLCGTTAS   179

SEQ ID NO: 5            moltype = AA  length = 442
FEATURE                 Location/Qualifiers
source                  1..442
                        mol_type = protein
                        organism = synthetic construct
SEQUENCE: 5
MYQSLAMAAN HGPPPGAYEA GGPGAFMHGA GAASSPVYVP TPRVPSSVLG LSYLQGGGAG  60
SASGGASGGS SGGAASGAGP GTQQGSPGWS QAGADGAAYT PPPVSPRFSF PGTTGSLAAA  120
AAAAAAREAA AYSSGGGAAG AGLAGREQYG RAGFAGSYSS PYPAYMADVG ASWAAAAAAS  180
AGPFDSPVLH SLPGRANPAA RHPNLDMFDD FSEGRECVNC GAMSTPLWRR DGTGHYLCNA  240
CGLYHKMNGI NRPLIKPQRR LSASRRVGLS CANCQTTTTT LWRRNAEGEP VCNACGLYMK  300
LHGVPRPLAM RKEGIQTRKR KPKNLNKSKT PAAPSGSESL PPASGASSNS SNATTSSSEE  360
MRPIKTEPGL SSHYGHSSSV SQTFSVSAMS GHGPSIHPVL SALKLSPQGY ASPVSQSPQT  420
SSKQDSWNSL VLADSHGDII TA                                          442
```

METHODS AND COMPOSITIONS FOR PRODUCING GRANULOSA-LIKE CELLS

CROSS-REFERENCE TO RELATED APPLICATIONS

This application is a continuation of and claims priority under 35 U.S.C. § 120 to U.S. patent application Ser. No. 18/852,012, filed Sep. 27, 2024, which is a national stage filing under 35 U.S.C. § 371 of International PCT Application No. PCT/US2023/065140, filed Mar. 30, 2023, which claims the benefit under 35 U.S.C. § 119(e) of U.S. Provisional Application No. 63/326,640, filed Apr. 1, 2022, and U.S. Provisional Application No. 63/444,108, filed Feb. 8, 2023, each of which is hereby incorporated by reference in its entirety.

REFERENCE TO AN ELECTRONIC SEQUENCE LISTING

The content of the electronic sequence listing (H049870758US03-SEQ-KVC.xml; Size: 7,426 bytes; and Date of Creation: Oct. 15, 2025) is herein incorporated by reference in its entirety.

BACKGROUND

Granulosa cells are specialized cells that, upon maturation, provide critical steroids and growth hormones to the developing oocyte. Granulosa cells surround developing oocytes and participate in maintaining a potential pregnancy by modulating hormone levels. Granulosa cell dysfunction forms the basis of many forms of human female infertility, yet efficient methods for generating granulosa in vitro remain elusive.

SUMMARY

The present disclosure relates, at least in part, to methods and compositions for generating granulosa in vitro from pluripotent stem cells (PSCs). The present disclosure provides experimental data demonstrating, unexpectedly, that overexpression of certain transcription factors, for example, Nuclear Receptor Subfamily 5 Group A Member 1 (NR5A1) and a Runt-Related Transcription Factor (RUNX) family member (e.g., RUNX1 and/or RUNX2), is sufficient to generate granulosa (e.g., AMHR2+, CD82+, FOXL2+, and/or EPCAM− granulosa-like cells) from iPSCs in as few as 5 to 7 days.

Some aspects of the present disclosure provide a PSC comprising: an engineered polynucleotide comprising an open reading frame encoding a protein selected from NR5A1 and a RUNX family protein.

In some embodiments, the PSC comprises the engineered polynucleotide comprising an open reading frame encoding NR5A1.

In some embodiments, the PSC comprises the engineered polynucleotide comprising an open reading frame encoding a RUNX family protein.

In some embodiments, the RUNX family protein is RUNX1.

In some embodiments, the RUNX family protein is RUNX2.

In some embodiments, the PSC expresses or overexpresses: NR5A1; RUNX1; RUNX2; NR5A1 and RUNX1; NR5A1 and RUNX2; or NR5A1, RUNX1, and RUNX2.

In some embodiments, the PSC further comprises an engineered polynucleotide comprising an open reading frame encoding a Transcription factor 21 (TCF21) protein.

In some embodiments, the PSC expresses or overexpresses TCF21.

In some embodiments, the PSC comprises the engineered polynucleotide comprising an open reading frame encoding GATA Binding Protein 4 (GATA4).

In some embodiments, the PSC expresses or overexpresses GATA4.

In some embodiments, the open reading frame of the engineered polynucleotide is operably linked to a heterologous promoter.

In some embodiments, the heterologous promoter is an inducible promoter.

Other aspects of the present disclosure provide a PSC comprising: a protein selected from NR5A1 and a RUNX family protein, wherein the protein is overexpressed.

In some embodiments, the PSC expresses or overexpresses: NR5A1; RUNX1; RUNX2; NR5A1 and RUNX1; NR5A1 and RUNX2; or NR5A1, RUNX1, and RUNX2.

In some embodiments, the PSC further comprises a TCF21 protein.

In some embodiments, the PSC expresses or overexpresses TCF21.

In some embodiments, the PSC further comprises a GATA4 protein.

In some embodiments, the PSC expresses or overexpresses GATA4.

In some embodiments, the PSC is a human PSC.

In some embodiments, the PSC is an induced PSC (iPSC).

In some embodiments, the PSC comprises 1-20, optionally 8-10, copies of the engineered polynucleotide comprising the open reading frame encoding the protein selected from NR5A1 and a RUNX family protein (e.g., RUNX1 and/or RUNX2).

Further aspects of the present disclosure provide a composition comprising: a population of the PSC of any one of the preceding paragraphs or described elsewhere herein.

In some embodiments, the population comprises at least 10,000/cm$^2$ of the PSC.

Some aspects of the present disclosure provide a method, comprising: culturing, in culture media, a population of PSCs to produce an expanded population of PSCs; and expressing in PSCs of the expanded population a protein selected from NR5A1 and a RUNX family protein to produce granulosa-like cells.

In some embodiments, the PSCs of the expanded population comprise an engineered polynucleotide comprising an open reading frame encoding NR5A1.

In some embodiments, the PSCs of the expanded population comprise an engineered polynucleotide comprising an open reading frame encoding a RUNX family protein.

In some embodiments, the RUNX family protein is RUNX1.

In some embodiments, the RUNX family protein is RUNX2.

In some embodiments, the PSCs of the expanded population further comprise an engineered polynucleotide comprising an open reading frame encoding a TCF21 protein.

In some embodiments, the PSCs of the expanded population further comprise an engineered polynucleotide comprising an open reading frame encoding a GATA4 protein.

In some embodiments, the open reading frame of the engineered polynucleotide is operably linked to a heterologous promoter.

In some embodiments, the heterologous promoter is an inducible promoter.

In some embodiments, the population comprises $1\times10^2$-$1\times10^7$ PSCs.

In some embodiments, the population of PSCs is cultured for about 4-10 days. For example, the population of PSCs may be cultured for about 6 days.

In some embodiments, the granulosa-like cells are AMHR2+, CD82+, FOXL2+, and/or EPCAM.

Other aspects of the present disclosure provide a method comprising: (a) delivering to PSCs an engineered polynucleotide comprising an inducible promoter operably linked to an open reading frame encoding a protein selected from NR5A1 and a RUNX family protein;

(b) culturing the PSCs in feeder-free, serum-free culture media to produce an expanded population of PSCs; and (c) culturing PSCs of the expanded population in a series of induction media comprising an inducing agent to produce AMHR2+, CD82+, FOXL2+, and/or EPCAM granulosa-like cells.

In some embodiments, the method comprises delivering to PSCs (i) an engineered polynucleotide comprising an inducible promoter operably linked to an open reading frame encoding NR5A1 and (i) an engineered polynucleotide comprising an inducible promoter operably linked to an open reading frame encoding a RUNX family protein.

In some embodiments, the RUNX family protein is RUNX1.

In some embodiments, the RUNX family protein is RUNX2.

In some embodiments, the engineered polynucleotide is a transposon and the delivering further comprises delivering a transposase to the PSCs.

In some embodiments, the inducible promoter is a chemically-inducible promoter, optionally a doxycycline-inducible promoter.

In some embodiments, the feeder-free, serum-free culture media of (b) comprises a solubilized basement membrane preparation extracted from the Engelbreth-Holm-Swarm (EHS) mouse sarcoma.

In some embodiments, the solubilized basement membrane preparation comprises extracellular matrix (ECM) proteins and growth factors.

In some embodiments, the ECM proteins are selected from Laminin, Collagen IV, heparan sulfate proteoglycans, and entactin/nidogen.

In some embodiments, the feeder-free, serum-free culture media of (b) comprises growth factors selected from recombinant human basic fibroblast growth factor (rh bFGF) and recombinant human transforming growth factor β (rh TGFβ).

In some embodiments, the culturing of (b) is for about 6-24 hours.

In some embodiments, the PSCs of the expanded population of (c) are cultured at a density of about 10,000 cells/cm$^2$ to about 20,000 cells/cm$^2$.

In some embodiments, the culturing of (c) comprises culturing the PSCs in a first induction media and culturing the PSCs in a second induction media.

In some embodiments, the first induction media comprises one or more of L-alanyl-L-glutamine, antibiotic (e.g., penicillin and/or streptomycin), Dulbecco's Modified Eagle Medium (DMEM)/F-12, Advanced RPMI (Roswell Park Memorial Institute) 1640 Medium, a glycogen synthase kinase (GSK) 3 inhibitor, a small molecule or protein inhibitor of the BMP signaling pathway, a small molecule ROCK inhibitor, and an inducing agent (e.g., doxycycline).

In some embodiments, the culturing the PSCs is a first induction media is for about 36 to about 60 hours, optionally about 48 hours.

In some embodiments, the second induction media comprises one or more of L-alanyl-L-glutamine, antibiotic (e.g., penicillin and/or streptomycin), Advanced RPMI 1640 Medium, DMEM/F-12, and an inducing agent (e.g., doxycycline).

In some embodiments, the culturing the PSCs in a second induction media is for about 96 to about 144 hours, optionally about 120 hours.

In some embodiments, the second induction media is removed and replaced with fresh second induction media at about 24-hour intervals.

Further aspects of the present disclosure provide a granulosa-like cell produced by the method of any one of the preceding claims.

The details of one or more embodiments of the invention are set forth in the description below. Other features or advantages of the present invention will be apparent from the following drawings and detailed description of several embodiments, and also from the appended claims.

Some aspects provide an ovarian organoid comprising granulosa-like cells of any one of the preceding claims and human primordial germ cell-like cells (hPGCLCS).

In some embodiments, a method of any one of the preceding paragraphs further comprising combining the granulosa-like cells with hPGCLCS to form an ovarian organoid.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 2 shows a TF combinatorial screen. Various combinations of TF expression plasmids were introduced into FOXL2-tdTomato reporter iPSCs. The iPSCs were then plated in differentiation medium (DMEM/F12, 10% KSR, 1 μg/mL doxycycline). During the first 2 days the cells were additionally treated with 3 μM CHIR99021 and 10 μM Y-27632. After 5 days of differentiation the cells were dissociated and analyzed by flow cytometry to measure the proportion of AMHR2+ FOXL2+ CD82+ EPCAM− granulosa-like cells. A second replicate was treated with androstenedione (500 ng/mL) and FSH (0.15 IU/mL) from days 4 to 6 of differentiation. Estradiol production was measured by ELISA.

FIG. 3 shows transcriptional characterization of granulosa-like cells. FOXL2+ cells generated by TF-mediated differentiation were analyzed by RNA-seq. TPM values for known markers of gonadal/granulosa, adrenal, and pluripotent cells were compared between male fetal gonad, primordial and primary granulosa cells, sorted FOXL2+ cells, COV434 ovarian tumor cells, and iPSCs. Values are the averages of at least two biological replicates.

FIG. 5A shows that granulosa-like cells produce estradiol in the presence of androstenedione and either FSH or forskolin (FK). Results are shown from nine monoclonal populations of granulosa-like cells (n=2 biological replicates for each of 9 clones, error bars are 95% CI), as well as the COV434 and KGN human ovarian cancer cell lines (controls), HGL5 immortalized primary human granulosa cells, and primary adult mouse granulosa cells. Asterisks mark lines where FSH production significantly (2-tailed t-test, p<.05) increased upon stimulation. Exact p-values are given in the Source Data. Monoclonal lines of iPSCs bearing integrated TFs (NR5A1, TCF21, GATA4, RUNX1) were generated by picking single colonies from a polyclonal population. These lines were then subjected to the 5-day granulosa differentiation protocol. Cells were subsequently treated with androstenedione (500 ng/ml) for 24 hours in the presence or absence of FSH (0.25 IU/mL) and/or forskolin (100 μM). Estradiol production was measured by ELISA. Three out of four lines showed hormone-responsive estradiol production, whereas the fourth line (found by PCR to be lacking RUNX1) constitutively produced high levels of estradiol. FIG. 5B shows that ovaroids produce both estradiol and progesterone. Estradiol production requires androstenedione and is stimulated by FSH. Results are shown for ovaroids formed with six different monoclonal samples of granulosa-like cells (n=1 sample per ovaroid per condition), at 3 days post aggregation.

FIG. 8A shows expression (log 2 CPM) of selected granulosa (FOXL2), stroma/theca (NR2F2), and germ cell (PRDM1) markers. FIG. 8B shows Leiden clustering shows four main clusters; the expression (log 2 CPM) of marker genes is plotted for each. FIG. 8C shows mapping of cells onto a human fetal ovary reference atlas and assignment of cell types. FIG. 8D shows the proportion of somatic cell types, germ cells, $DAZL^+$ cells, and $DDX4^+$ cells in ovaroids from each day.

DETAILED DESCRIPTION

Figure 1:
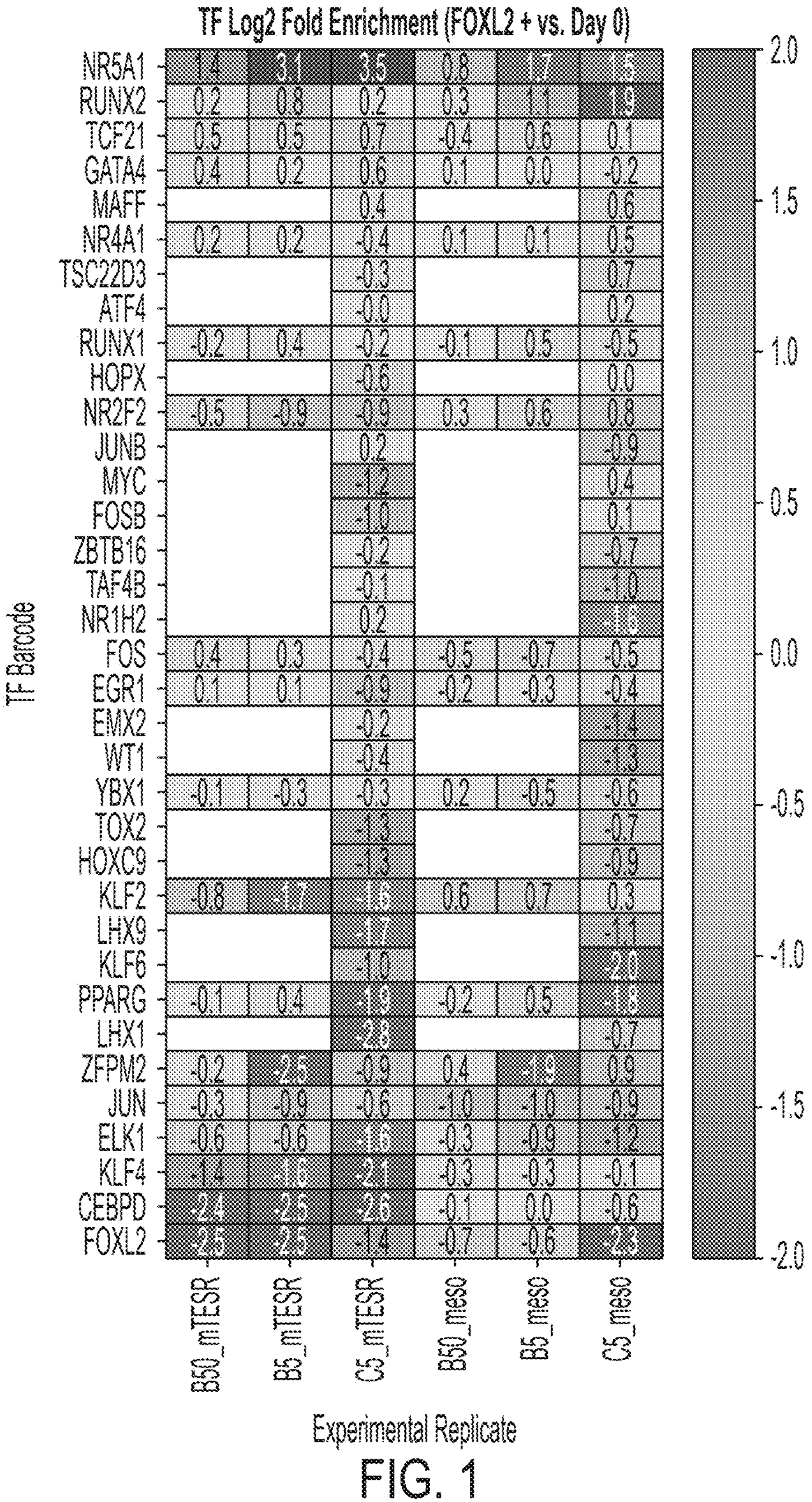
FIG. 1 shows barcode enrichment screening for TFs activating FOXL2 expression. TF expression plasmids were introduced into FOXL2-tdTomato reporter iPSCs. Three TF pools were evaluated: C5, containing 5 fmol total of all TFs (equimolar mix); B5, containing 5 fmol total of a subset of TFs; and B50, containing 50 fmol total of the same subset. After nucleofection and puromycin selection, cells were treated with doxycycline to induce TF expression, either in pluripotency-supporting mTeSR™ Plus medium or mesoderm-inducing medium. After 5 days, FOXL2+ cells were isolated by FACS and DNA was extracted. Barcode frequencies were compared between FOXL2+ cells and the initial population of cells before TF expression.

Ovaria granulosa cells are important for many aspects of female reproduction, including the support of oocyte development and hormonal signaling during the menstrual cycle. Current in vitro models, including primary human or mouse granulosa cells and granulosa cell tumor lines, are inadequate for studying these processes (Havelock et al. 2004). For example, the COV434 ovarian tumor line, commonly used as a model for granulosa cells (Zhang 2000), lacks transcriptional and phenotypic characteristics of bona fide granulosa cells. Previously reported protocols for differentiating induced pluripotent stem cells (iPSCs) into granulosa-like cells are either low-yielding (Lan et al. 2013; Lipskind et al. 2018) or only applicable to mouse cells (Yoshino et al. 2021). Aspects of the present disclosure relate to a robust, scalable method of using direct transcription factor overexpression to mediate differentiation of iPSCs to produce granulosa-like cells that are $AMHR2^+$ (Anti-Mullerian Hormone Receptor Type 2), $CD82^+$ (Cluster of Differentiation 82), $FOXL2^+$ (Forkhead Box L2), and/or EPCAM (Epithelial Cellular Adhesion Molecule) in about 4 to about 10 days. It should be understood that the term "granulosa-like cells" encompasses cells that express granulosa-specific markers, such as AMHR2, CD82, and/or FOXL2 and/or do not express EPCAM, and exhibit other characteristics of naturally-occurring granulosa.

Aspects of the present disclosure relate to a pluripotent stem cell (PSC) comprising: an engineered polynucleotide comprising an open reading frame encoding a protein selected from Nuclear Receptor Subfamily 5 Group A Member 1 (NR5A1) and a Runt-Related Transcription Factor (RUNX) family protein. In some embodiments, the engineered polynucleotide comprising an open reading frame encoding NR5A1. In some embodiments, the engineered polynucleotide comprising an open reading frame encoding a RUNX family protein. In some embodiments, the RUNX family protein is Runt-Related Transcription Factor 1 (RUNX1). In some embodiments, the RUNX family protein is Runt-Related Transcription Factor 2 (RUNX2).

Granulosa-Like Cells

Some aspects of the present disclosure provide granulosa-like cells and methods of producing such cells. A granulosa cell or follicular cell is a somatic cell of the sex cord that is closely associated with the developing female gamete (oocyte/egg) in the ovary of mammals. In the primordial ovarian follicle, and later in follicle development (folliculogenesis), granulosa cells advance to form a multilayered cumulus oophorus surrounding the oocyte in the preovulatory or antral (Graafian) follicle. The major functions of granulosa cells include the production of sex steroids, as well as myriad growth factors thought to interact with the oocyte during its development. The sex steroid production begins with follicle-stimulating hormone (FSH) from the anterior pituitary, stimulating granulosa cells to convert androgens (coming from the thecal cells) to estradiol by aromatase during the follicular phase of the menstrual cycle. After ovulation the granulosa cells turn into granulosa lutein cells that produce progesterone. The progesterone may maintain a potential pregnancy and causes production of a thick cervical mucus that inhibits sperm entry into the uterus.

There are two types of granulosa cells: cumulus cells (CC) and mural granulosa cells (MGC). Cumulus cells surround the oocyte. They provide nutrients to the oocyte and influence the development of the oocyte in a paracrine fashion. Mural granulosa cells line the follicular wall and surround the fluid-filled antrum. The oocyte secretes factors that determine the functional differences between CCs and MGGs. CCs primarily support growth and development of the oocyte whereas MGCs primarily serve an endocrine function and support the growth of the follicle. Cumulus cells aid in oocyte development and show higher expression of SLC38A3, a transporter for amino acids, and Aldoa, Eno1, Ldh1, Pfkp, Pkm2, and Tpi1, enzymes responsible for glycolysis. MGCs are more steroidogenically active and have higher levels of mRNA expression of steroidogenic enzymes such as cytochrome P450. MGCs produce an increasing amount of estrogen which leads to the LH surge. Following the LH surge, cumulus cells undergo cumulus expansion, in which they proliferate at a ten-fold higher rate than MGCs in response to FSH. During expansion CCs also produce a mucified matrix required for ovulation.

Granulosa cells express a number of different biomarkers that can be used to distinguish granulosa and granulosa-like cells from other cell types. For example, granulosa cells are typically positive for Anti-Mullerian Hormone Receptor Type 2 (AMHR2) (AMHR2+), CD82 molecule (CD82+), Forkhead Box L2 (FOXL2+), and negative for Epithelial Cell Adhesion Molecule (EPCAM−). Thus, in some embodiments, the granulosa-like cells produced by the methods provided herein are AMHR2+, CD82+, FOXL2+, and/or EPCAM− granulosa-like cells (i.e., cells that express AMHR2, CD82, and/or FOXL2 protein but do not express detectable levels of EPCAM).

There are other characteristics of granulosa-like cells that distinguish them from non-granulosa-like cells including, but not limited to, expression of combinations of adhesion proteins such as adherens (B-catenin, a,catenin, N-cadherin, Nectins 1-3) as well as tight junctions (JAM-A, cingulin), desmosomes (dsg2, Dsc2) and linkers (afadin, ZO-1,2 and ZONAB). Furthermore, granulosa-like cells are distinguished by biosynthesis of combinations of estradiol, progesterone, and AMH.

Pluripotent Stem Cells

The granulosa-like cells provided herein are differentiated from pluripotent stem cells. Pluripotent stem cells are cells that have the capacity to self-renew by dividing, and to develop into the three primary germ cell layers of the early embryo (e.g., ectoderm, endoderm, and mesoderm), and therefore into all cells of the adult body, but not extra-embryonic tissues such as the placenta (Shi et al. 2017).

Non-limiting examples of pluripotent stem cells include induced pluripotent cell (iPSCs), "true" embryonic stem cell (ESCs) derived from embryos, embryonic stem cells made by somatic cell nuclear transfer (ntESCs), and embryonic stem cells from unfertilized eggs (parthenogenesis embryonic stem cells, or pESCs). In some embodiments, a pluripotent cell is a human pluripotent cell.

In some embodiments, a pluripotent stem cell is an embryonic stem cell, such as a human embryonic stem cell. "Embryonic stem cell" is a general term for pluripotent stem cells that are made using embryos or eggs, rather than for cells genetically reprogrammed from the body. As used herein, "ESCs" encompass true ESCs, ntESCs, and pESCs.

In other embodiments, a pluripotent stem cell is an induced pluripotent stem cell, such as a human induced pluripotent stem cell. iPSCs may be derived from skin or blood cells that have been reprogrammed back into an embryonic-like pluripotent state that enables the development of an unlimited source of any type of human cell.

Some aspects of the present disclosure provide a PSC comprising: a protein selected from NR5A1 and a RUNX family protein (e.g., RUNX1 and/or RUNX2), wherein the protein is expressed or overexpressed. In some embodiments, the PSC further comprises a TCF21 protein. In some embodiments, the protein is expressed at a level that is at least 5%, at least 10%, at least 15%, at least 20%, at least 25%, at least 50%, or at least 100% higher than a control level. In some embodiments, the PSC further comprises a GATA4 protein. In some embodiments, the protein is expressed at a level that is at least 5%, at least 10%, at least 15%, at least 20%, at least 25%, at least 50%, or at least 100% higher than a control level. In some embodiments, a control level is an endogenous level of the protein, for example in a naturally-occurring pluripotent stem cell. In some embodiments, a PSC comprises NR5A1. In some embodiments, a PSC expresses or overexpresses NR5A1. In some embodiments, a PSC comprises a RUNX family protein (e.g., RUNX1 and/or RUNX2). In some embodiments, a PSC expresses or overexpresses a RUNX family protein (e.g., RUNX1 and/or RUNX2). In some embodiments, a PSC comprises RUNX1. In some embodiments, a PSC expresses or overexpresses RUNX1. In some embodiments, a PSC comprises RUNX2. In some embodiments, a PSC expresses or overexpresses RUNX2. In some embodiments, a PSC comprises TCF21. In some embodiments, a PSC expresses or overexpresses TCF21. In some embodiments, a PSC comprises GATA4. In some embodiments, a PSC expresses or overexpresses GATA4.

Data provided herein shows that combinatorial expression of NR5A1 and a RUNX family protein (e.g., RUNX1 and/or RUNX2) results in a 2-15 fold increase in efficiency of granulosa cell-like production, relative to a control, optionally wherein the control is efficiency of granulosa cell-like production in a PSC expressing only one of NR5A1 or a RUNX family protein (e.g., RUNX1 and/or RUNX2). In some embodiments, a PSC comprises NR5A1 and a RUNX family protein (e.g., RUNX1 and/or RUNX2). In some embodiments, a PSC expresses or overexpresses NR5A1 and a RUNX family protein (e.g., RUNX1 and/or RUNX2). In some embodiments, a PSC comprises NR5A1 and RUNX1. In some embodiments, a PSC expresses or overexpresses NR5A1 and RUNX1. In some embodiments, a PSC comprises NR5A1 and RUNX2. In some embodiments, a PSC expresses or overexpresses NR5A1 and RUNX2. In some embodiments, a PSC further comprises TCF21. In some embodiments, a PSC further expresses or overexpresses TCF21. In some embodiments, a PSC further comprises GATA4. In some embodiments, a PSC further expresses or overexpresses GATA4.

Transcription Factors

The granulosa-like cells provided herein are differentiated from pluripotent stem cells, in some embodiments, by expressing one or more (e.g., 2, 3, 4, 5, 6, 7, 8, or 9) transcription factors (i.e., a protein that controls the rate of transcription). Differentiation is the process by which an uncommitted cell or a partially committed cell commits to a specialized cell fate. Aspects of the present disclosure relate to the differentiation of uncommitted pluripotent stem cells into a granulosa-like cell fate.

In some embodiments, the transcription factors are selected from NR5A1 and a RUNX family protein (e.g., RUNX1 and/or RUNX2). In some embodiments, pluripotent stem cells, such as hPSCs or hiPSCs, are engineered to express or overexpress NR5A1. In some embodiments, pluripotent stem cells, such as hPSCs or hiPSCs, are engineered to express or overexpress a RUNX family protein (e.g., RUNX1 and/or RUNX2). In some embodiments, pluripotent stem cells, such as hPSCs or hiPSCs, are engineered to express or overexpress RUNX1. In some embodiments, pluripotent stem cells, such as hPSCs or hiPSCs, are engineered to express or overexpress RUNX2. In some embodiments, pluripotent stem cells, such as hPSCs or hiPSCs, are engineered to express or overexpress TCF21. In some embodiments, pluripotent stem cells, such as hPSCs or hiPSCs, are engineered to express or overexpress GATA4. In some embodiments, pluripotent stem cells, such as hPSCs or hiPSCs, are engineered to express or overexpress NR5A1 and a RUNX family protein (e.g., RUNX1 and/or RUNX2). In some embodiments, pluripotent stem cells, such as hPSCs or hiPSCs, are engineered to express or overexpress NR5A1 and RUNX1. In some embodiments, pluripotent stem cells, such as hPSCs or hiPSCs, are engineered to express or overexpress NR5A1 and RUNX2. In some embodiments, pluripotent stem cells, such as hPSCs or hiPSCs, are engineered to further express or overexpress TCF21. In some embodiments, pluripotent stem cells, such as hPSCs or hiPSCs, are engineered to further express or overexpress GATA4.

A cell "expressed" a particular protein if the level of the protein in the cell is detectable (e.g., using a known protein assay). A cell "overexpresses" a particular protein (e.g., engineered polynucleotide encoding the protein) if the level of the protein is higher than (e.g., at least 5%, at least 10%, or at least 20% higher than) the level of the protein expressed from an endogenous, naturally-occurring polynucleotide encoding the protein.

Engineered Polynucleotides and Polypeptides

The pluripotent stem cells of the present disclosure, in some embodiments, comprise engineered polynucleotides. An engineered polynucleotide is a nucleic acid (e.g., at least two nucleotides covalently linked together, and in some instances, containing phosphodiester bonds, referred to as a phosphodiester backbone) that does not occur in nature. Engineered polynucleotides include recombinant nucleic acids and synthetic nucleic acids. A recombinant nucleic acid is a molecule that is constructed by joining nucleic acids (e.g., isolated nucleic acids, synthetic nucleic acids or a combination thereof) from two different organisms (e.g., human and mouse). A synthetic nucleic acid is a molecule that is amplified or chemically, or by other means, synthesized. A synthetic nucleic acid includes those that are chemically modified, or otherwise modified, but can base pair with (bind to) naturally occurring nucleic acid molecules. Recombinant and synthetic nucleic acids also include those molecules that result from the replication of either of the foregoing.

An engineered polynucleotide may comprise DNA (e.g., genomic DNA, cDNA or a combination of genomic DNA and cDNA), RNA or a hybrid molecule, for example, where the nucleic acid contains any combination of deoxyribonucleotides and ribonucleotides (e.g., artificial or natural), and any combination of two or more bases, including uracil, adenine, thymine, cytosine, guanine, inosine, xanthine, hypoxanthine, isocytosine and isoguanine.

In some embodiments, a polynucleotide is a complementary DNA (cDNA). cDNA is synthesized from a single-stranded RNA (e.g., messenger RNA (mRNA) or microRNA (miRNA)) template in a reaction catalyzed by reverse transcriptase.

Engineered polynucleotides of the present disclosure may be produced using standard molecular biology methods (see, e.g., *Green and Sambrook, Molecular Cloning*, A Laboratory Manual, 2012, Cold Spring Harbor Press). In some embodiments, nucleic acids are produced using GIBSON ASSEMBLY® Cloning (see, e.g., Gibson, D. G. et al. *Nature Methods,* 343-345, 2009; and Gibson, D. G. et al. *Nature Methods,* 901-903, 2010, each of which is incorporated by reference herein). GIBSON ASSEMBLY® typically uses three enzymatic activities in a single-tube reaction: 5' exonuclease, the 3' extension activity of a DNA polymerase and DNA ligase activity. The 5' exonuclease activity chews back the 5' end sequences and exposes the complementary sequence for annealing. The polymerase activity then fills in the gaps on the annealed domains. A DNA ligase then seals the nick and covalently links the DNA fragments together. The overlapping sequence of adjoining fragments is much longer than those used in Golden Gate Assembly, and therefore results in a higher percentage of correct assemblies. Other methods of producing engineered polynucleotides may be used in accordance with the present disclosure.

In some embodiments, an engineered polynucleotide comprises a promoter operably linked to an open reading frame. A promoter is a nucleotide sequence to which RNA polymerase binds to initial transcription (e.g., ATG). Promoters are typically located directly upstream from (at the 5' end of) a transcription initiation site. In some embodiments, a promoter is a heterologous promoter. A heterologous promoter is not naturally associated with the open reading frame to which is it operably linked.

In some embodiments, a promoter is an inducible promoter. An inducible promoter may be regulated in vivo by a chemical agent, temperature, or light, for example. Inducible promoters enable, for example, temporal and/or spatial control of gene expression. Inducible promoters for use in accordance with the present disclosure include any inducible promoter described herein or known to one of ordinary skill in the art. Examples of inducible promoters include, without limitation, chemically/biochemically-regulated and physically-regulated promoters such as alcohol-regulated promoters, tetracycline-regulated promoters (e.g., anhydrotetracycline (aTc)-responsive promoters and other tetracycline responsive promoter systems, which include a tetracycline repressor protein (tetR), a tetracycline operator sequence (tetO) and a tetracycline transactivator fusion protein (tTA)), steroid-regulated promoters (e.g., promoters based on the rat glucocorticoid receptor, human estrogen receptor, moth ecdysone receptors, and promoters from the steroid/retinoid/thyroid 25 receptor superfamily), metal-regulated promoters (e.g., promoters derived from metallothionein (proteins that bind and sequester metal ions) genes from yeast, mouse and human), pathogenesis-regulated promoters (e.g., induced by salicylic acid, ethylene or benzothiadiazole (BTH)), temperature/heat-inducible promoters (e.g., heat shock promoters), and light-regulated promoters (e.g., light responsive promoters from plant cells). In some embodiments, the inducible promoter is a tetracycline-inducible promoter. In some embodiments, the inducible promoter is a doxycycline-inducible promoter. In other embodiments, a promoter is a constitutive promoter (active in vivo, unregulated).

An open reading frame is a continuous stretch of codons that begins with a start codon (e.g., ATG), ends with a stop codon (e.g., TAA, TAG, or TGA), and encodes a polypeptide, for example, a protein. An open reading frame is operably linked to a promoter if that promoter regulates transcription of the open reading frame.

Vectors used for delivery of an engineered polynucleotide include minicircles, plasmids, bacterial artificial chromosomes (BACs), and yeast artificial chromosomes. Transposon-based systems, such as the piggyBac™ system (e.g., Chen et al. Nature Communications. 2020; 11 (1): 3446), is also contemplated herein.

A pluripotent stem cells, in some embodiments, comprises an engineered polynucleotide comprising an open reading frame encoding a protein selected from NR5A1 and a RUNX family protein (e.g., RUNX1 and/or RUNX2). In some embodiments, the engineered polynucleotide comprises an open reading frame encoding NR5A1. In some embodiments, the engineered polynucleotide comprises an open reading frame encoding a RUNX family protein (e.g., RUNX1 and/or RUNX2). In some embodiments, the engineered polynucleotide comprises an open reading frame encoding RUNX1. In some embodiments, the engineered polynucleotide comprises an open reading frame encoding RUNX2. In some embodiments, the engineered polynucleotide comprises an open reading frame encoding TCF21. In some embodiments, the engineered polynucleotide comprises an open reading frame encoding GATA4.

In some embodiments, a pluripotent stem cell comprises an engineered polynucleotide comprising an open reading frame encoding NR5A1 and an engineered polynucleotide comprising an open reading frame encoding a RUNX family protein (e.g., RUNX1 and/or RUNX2). In some embodiments, a pluripotent stem cell comprises an engineered polynucleotide comprising an open reading frame encoding NR5A1 and an engineered polynucleotide comprising an open reading frame encoding RUNX1. In some embodiments, a pluripotent stem cell comprises an engineered polynucleotide comprising an open reading frame encoding NR5A1 and an engineered polynucleotide comprising an open reading frame encoding RUNX2. In some embodiments, a pluripotent stem cell further comprises an engineered polynucleotide comprising an open reading frame encoding TCF21. In some embodiments, a pluripotent stem cell further comprises an engineered polynucleotide comprising an open reading frame encoding GATA4.

An engineered polynucleotide encoding comprising an open reading frame encoding Nuclear Receptor Subfamily 5 Group A Member 1 (NR5A1) (e.g., UniprotKB Accession No. Q13285), in some embodiments, encodes a protein comprising the sequence of:

```
                                            (SEQ ID NO: 1)
MDYSYDEDLDELCPVCGDKVSGYHYGLLTCESCKGFFKRTVQNNKHYTCT

ESQSCKIDKTQRKRCPFCRFQKCLTVGMRLEAVRADRMRGGRNKFGPMYK

RDRALKQQKKAQIRANGFKLETGPPMGVPPPPPPAPDYVLPPSLHGPEPK

GLAAGPPAGPLGDFGAPALPMAVPGAHGPLAGYLYPAFPGRAIKSEYPEP

YASPPQPGLPYGYPEPFSGGPNVPELILQLLQLEPDEDQVRARILGCLQE

PTKSRPDQPAAFGLLCRMADQTFISIVDWARRCMVFKELEVADQMTLLQN

CWSELLVFDHIYRQVQHGKEGSILLVTGQEVELTTVATQAGSLLHSLVLR

AQELVLQLLALQLDRQEFVCLKFIILFSLDLKFLNNHILVKDAQEKANAA
```

-continued

```
LLDYTLCHYPHCGDKFQQLLLCLVEVRALSMQAKEYLYHKHLGNEMPRNN

LLIEMLQAKQT
```

An engineered polynucleotide encoding comprising an open reading frame encoding Runt-Related Transcription Factor 1 (RUNX1) (e.g., UniprotKB Accession No. Q01196), in some embodiments, encodes a protein comprising the sequence of:

```
                                            (SEQ ID NO: 2)
MRIPVDASTSRRFTPPSTALSPGKMSEALPLGAPDAGAALAGKLRSGDRS

MVEVLADHPGELVRTDSPNFLCSVLPTHWRCNKTLPIAFKVVALGDVPDG

TLVTVMAGNDENYSAELRNATAAMKNQVARFNDLRFVGRSGRGKSFTLTI

TVFTNPPQVATYHRAIKITVDGPREPRRHRQKLDDQTKPGSLSFSERLSE

LEQLRRTAMRVSPHHPAPTPNPRASLNHSTAFNPQPQSQMQDTRQIQPSP

PWSYDQSYQYLGSIASPSVHPATPISPGRASGMTTLSAELSSRLSTAPDL

TAFSDPRQFPALPSISDPRMHYPGAFTYSPTPVTSGIGIGMSAMGSATRY

HTYLPPPYPGSSQAQGGPFQASSPSYHLYYGASAGSYQFSMVGGERSPPR

ILPPCTNASTGSALLNPSLPNQSDVVEAEGSHSNSPTNMAPSARLEEAVW

RPY
```

An engineered polynucleotide encoding comprising an open reading frame encoding Runt-Related Transcription Factor 2 (RUNX2) (e.g., UniprotKB Accession No. Q13950), in some embodiments, encodes a protein comprising the sequence of:

```
                                            (SEQ ID NO: 3)
MASNSLFSTVTPCQQNFFWDPSTSRRFSPPSSSLQPGKMSDVSPVVAAQQ

QQQQQQQQQQQQQQQQQQQQQEAAAAAAAAAAAAAAAAAVPRLRPPHDNR

TMVEIIADHPAELVRTDSPNFLCSVLPSHWRCNKTLPVAFKVVALGEVPD

GTVVTVMAGNDENYSAELRNASAVMKNQVARFNDLRFVGRSGRGKSFTLT

ITVFTNPPQVATYHRAIKVTVDGPREPRRHRQKLDDSKPSLFSDRLSDLG

RIPHPSMRVGVPPQNPRPSLNSAPSPFNPQGQSQITDPRQAQSSPPWSYD

QSYPSYLSQMTSPSIHSTTPLSSTRGTGLPAITDVPRRISDDDTATSDFC

LWPSTLSKKSQAGASELGPFSDPRQFPSISSLTESRFSNPRMHYPATFTY

TPPVTSGMSLGMSATTHYHTYLPPPYPGSSQSQSGPFQTSSTPYLYYGTS

SGSYQFPMVPGGDRSPSRMLPPCTTTSNGSTLLNPNLPNQNDGVDADGSH

SSSPTVLNSSGRMDESVWRPY
```

An engineered polynucleotide encoding comprising an open reading frame encoding Transcription factor 21 (TCF21) (e.g., UniprotKB Accession No. 043680), in some embodiments, encodes a protein comprising the sequence of:

```
                                            (SEQ ID NO: 4)
MSTGSLSDVEDLQEVEMLECDGLKMDSNKEFVTSNESTEESSNCENGSPQ

KGRGGLGKRRKAPTKKSPLSGVSQEGKQVQRNAANARERARMRVLSKAFS
```

-continued

RLKTTLPWVPPDTKLSKLDTLRLASSYIAHLRQILANDKYENGYIHPVNL

TWPFMVAGKPESDLKEVVTASRLCGTTAS

An engineered polynucleotide encoding comprising an open reading frame encoding GATA Binding Protein 4 (GATA4) (e.g., UniprotKB Accession No. P43694), in some embodiments, encodes a protein comprising the sequence of:

(SEQ ID NO: 5)

MYQSLAMAANHGPPPGAYEAGGPGAFMHGAGAASSPVYVPTPRVPSSVLG

LSYLQGGGAGSASGGASGGSSGGAASGAGPGTQQGSPGWSQAGADGAAYT

PPPVSPRFSFPGTTGSLAAAAAAAAAREAAAYSSGGGAAGAGLAGREQYG

RAGFAGSYSSPYPAYMADVGASWAAAAAASAGPFDSPVLHSLPGRANPAA

RHPNLDMEDDESEGRECVNCGAMSTPLWRRDGTGHYLCNACGLYHKMNGI

NRPLIKPQRRLSASRRVGLSCANCQTTTTTLWRRNAEGEPVCNACGLYMK

LHGVPRPLAMRKEGIQTRKRKPKNLNKSKTPAAPSGSESLPPASGASSNS

SNATTSSSEEMRPIKTEPGLSSHYGHSSSVSQTFSVSAMSGHGPSIHPVL

SALKLSPQGYASPVSQSPQTSSKQDSWNSLVLADSHGDIITA

The number of copies of an engineered polynucleotide delivered to a PSC may vary. In some embodiments, a PSC comprises 1-20 copies of an engineered polynucleotide. For example, and PSC may comprise 1-15, 1-10, 2-10, 2-15, 2-10, 5-20, 5-15, or 5-10 copies of an engineered polynucleotide. In some embodiments, a PSC comprises 8-10 copies of an engineered polynucleotide. Greater than 20 copies are also contemplated herein.

Methods of Producing Granulosa-Like Cells

The methods of producing granulosa-like cells provided herein, in some aspects, comprises culturing, in culture media, a population of pluripotent stem cells (PSCs) to produce an expanded population of PSCs; and expressing in PSCs of the expanded population a protein selected from NR5A1 and a RUNX family protein (e.g., RUNX1 and/or RUNX2) to produce granulosa-like cells. In some embodiments, the methods further comprising expressing in PSCs of the expanded population a TCF21 protein. In some embodiments, the methods further comprising expressing in PSCs of the expanded population a GATA4 protein.

In some embodiments, the PSCs of the expanded population comprise an engineered polynucleotide comprising an open reading frame encoding NR5A1. In some embodiments, the PSCs of the expanded population comprise an engineered polynucleotide comprising an open reading frame encoding a RUNX family protein (e.g., RUNX1 and/or RUNX2). In some embodiments, the PSCs of the expanded population comprise an engineered polynucleotide comprising an open reading frame encoding RUNX1. In some embodiments, the PSCs of the expanded population comprise an engineered polynucleotide comprising an open reading frame encoding RUNX2. In some embodiments, the PSCs of the expanded population comprise an engineered polynucleotide comprising an open reading frame encoding TCF21. In some embodiments, the PSCs of the expanded population comprise an engineered polynucleotide comprising an open reading frame encoding GATA4.

In some embodiments, the open reading frame of the engineered polynucleotide is operably linked to a heterologous promoter.

In some embodiments, the heterologous promoter is an inducible promoter, non-limiting examples of which are provided elsewhere herein.

The population a starting population comprises about $1\times10^{2}$-$1\times10^{10}$, about $1\times10^{2}$-$1\times10^{9}$, about $1\times10^{2}$-$1\times10^{8}$, or about $1\times10^{2}$-$1\times10^{7}$ PSCs. In some embodiments, the population comprises about $1\times10^{3}$-$1\times10^{8}$ or about $1\times10^{3}$-$1\times10^{7}$ PSCs. In some embodiments, the population comprises about $1\times10^{4}$-$1\times10^{7}$ or about $1\times10^{5}$-$1\times10^{6}$ PSCs. In some embodiments, the population comprises about $1\times10^{1}$ PSCs, about $1\times10^{2}$ PSCs, about $1\times10^{3}$ PSCs, about $1\times10^{4}$ PSCs, about $1\times10^{5}$ PSCs, about $1\times10^{6}$ PSCs, about $1\times10^{7}$ PSCs, about $1\times10^{8}$ PSCs, about $1\times10^{9}$ PSCs, or about $1\times10^{10}$ PSCs.

In some embodiments, the population of PSCs is cultured for about 4 to about 10 days, about 4 to about 9 days, about 4 to about 8 days, about 4 to about 7 days, about 4 to about 6 days, about 5 to about 10 days, about 5 to about 9 days, about 5 to about 8 days, about 5 to about 7 days, or about 5 to about 6 days. In some embodiments, the population of PSCs is cultured for about 4 days, about 5 days, about 6 days, about 7 days, about 8 days, about 9 days, or about 10 days.

Some methods of the present disclosure provide methods comprising (a) delivering to PSCs an engineered polynucleotide comprising an inducible promoter operably linked to an open reading frame encoding a protein selected from NR5A1 and a RUNX family protein (e.g., RUNX1 and/or RUNX2); (b) culturing the PSCs in feeder-free, serum-free culture media to produce an expanded population of PSCs; and (c) culturing PSCs of the expanded population in a series of induction media comprising an inducing agent to produce AMHR2+, CD82+, FOXL2+, and/or EPCAM− granulosa-like cells. In some embodiments, the series of induction media comprises a first, a second, a third, and a fourth induction media. In some embodiments, an engineered polynucleotide comprising an inducible promoter operably linked to an open reading frame encoding a TCF21 protein is also delivered to the PCSs (e.g., in step (a)). In some embodiments, an engineered polynucleotide comprising an inducible promoter operably linked to an open reading frame encoding a GATA4 protein is also delivered to the PCSs (e.g., in step (a)).

In some embodiments, the PSCs are cultured in feeder-free, serum-free culture media for about 6 to about 24 hours. For example, the PSC may be cultured in feeder-free, serum-free culture media for about, 6 to about 12 hours. In some embodiments, the PSCs are cultured in feeder-free, serum-free culture media for about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or about 24 hours.

In some embodiments, the expanded population of PSCs comprises at least $5\times10^{3}$ PSCs. For example, the expanded population (e.g., at the time of induction) may comprise at least $1\times10^{4}$, at least $1\times10^{5}$, at least $1\times10^{6}$, or at least $1\times10^{7}$ PSCs. In some embodiments, the expanded population of PSCs comprises about $5\times10^{3}$ PSCs to about $1\times10^{7}$ PSCs.

In some embodiments, PSCs of the expanded population are cultured at a density of about 10,000 cells/$cm^2$ to about 30,000 cells/$cm^2$. In some embodiments, PSCs of the expanded population are cultured at a density of about 10,000 cells/$cm^2$ to about 25,000 cells/$cm^2$. In some embodiments, PSCs of the expanded population are cultured at a density of about 10,000 cells/$cm^2$ to about 20,000 cells/cm$^2$. In some embodiments, PSCs of the expanded population are cultured at a density of about 10,000 cells/cm$^2$ to about 15,000 cells/cm$^2$. In some embodiments, PSCs of the expanded population are cultured at a density of about 15,000 cells/cm$^2$ to about 30,000 cells/cm$^2$. In some embodiments, PSCs of the expanded population are cultured at a density of about 15,000 cells/cm$^2$ to about 25,000 cells/cm$^2$. In some embodiments, PSCs of the expanded population are cultured at a density of about 15,000 cells/cm$^2$ to about 20,000 cells/cm$^2$. In some embodiments, PSCs of the expanded population are cultured at a density of at least 10,000/cm$^2$, at least 15,000/cm$^2$, at least 20,000/cm$^2$, at least 25,000/cm$^2$, or at least 30,000/cm$^2$.

In some embodiments, PSCs of the expanded population are cultured for no longer than 10 days, no longer than 9 days, no longer than 8 days, no longer than 7 days, no longer than 6 days, no longer than 5 days, or no longer than 4 days. For example, PSCs of the expanded population may be cultured for about 4 to about 10 days, about 4 to about 9 days, about 4 to about 8 days, about 4 to about 7 days, about 4 to about 6 days, about 5 to about 10 days, about 5 to about 9 days, about 5 to about 8 days, about 5 to about 7 days, or about 5 to about 6 days. In some embodiments, PSCs of the expanded population are cultured for about 4 days, about 5 days, about 6 days, about 7 days, about 8 days, about 9 days, or about 10 days.

In some embodiments, PSCs of the expanded population are cultured in a first induction media for about 36 to about 60 hours. For example, the PSC may be cultured in a first induction media for about 36 to about 54 hours, about 36 to about 48 hours, about 42 to about 60 hours, about 42 to about 54 hours, about 42 to about 48 hours, about 48 to about 60 hours, or about 48 to about 54 hours. In some embodiments, the PSCs are cultured in a first induction media for about 36 hours, about 42 hours, about 48 hours, about 54 hours, or about 60 hours.

In some embodiments, PSCs of the expanded population are cultured in a second induction media for about 96 to about 144 hours. For example, the PSC may be cultured in a second induction media for about 96 to about 132 hours, about 96 to about 120 hours, about 96 to about 108 hours, about 108 to about 144 hours, about 108 to about 132 hours, about 108 to about 120 hours, about 120 to about 144 hours, or about 120 to about 132 hours. In some embodiments, the PSCs are cultured in a second induction media for about 96 hours, about 108, about 120 hours, about 132 hours, or about 144 hours.

Culturing in the second induction media comprises, in some embodiments, several (one or more) media changes. For example, the second induction media may be removed and replaced with new (fresh) second indication media every (about) 12 hours, every 24, hours, every 36 hours, or every 48 hours. In some embodiments, the second induction media is changed every (about) 24 hours.

Transfection Methods

The engineered polynucleotide of the present disclosure may be delivered to a PSC using any one or more transfection method, including chemical transfection methods, viral transduction methods, and electroporation.

In some embodiments, an engineered polynucleotide is delivered on a vector. A vector is any vehicle, for example, a virus or a plasmid, that is used to transfer a desired polynucleotide into a host cell, such as a PSC. In some embodiments, the vector is a viral vector. In some embodiments, a viral vector is not a naturally occurring viral vector. The viral vector may be from adeno-associated virus (AAV), adenovirus, herpes simplex virus, lentiviral, retrovirus, varicella, variola virus, hepatitis B, cytomegalovirus, JC polyomavirus, BK polyomavirus, monkeypox virus, Herpes Zoster, Epstein-Barr virus, human herpes virus 7, Kaposi's sarcoma-associated herpesvirus, or human parvovirus B 19. Other viral vectors are encompassed by the present disclosure.

In some embodiments, a viral vector is an AAV vector. AAV is a small, non-enveloped virus that packages a single-stranded linear DNA genome that is approximately 5 kb long and has been adapted for use as a gene transfer vehicle (Samulski, R J et al., Annu Rev Virol. 2014; 1 (1): 427-51). The coding regions of AAV are flanked by inverted terminal repeats (ITRs), which act as the origins for DNA replication and serve as the primary packaging signal (McLaughlin, S K et al. Virol. 1988; 62 (6): 1963-73; Hauswirth, W W et al. 1977: 78 (2): 488-99). Thus, an AAV vector typically includes ITR sequences. Both positive and negative strands are packaged into virions equally well and capable of infection (Zhong, L et al. Mol Ther. 2008; 16 (2): 290-5; Zhou, X et al. Mol Ther. 2008: 16 (3): 494-9; Samulski, R J et al. Virol. 1987: 61 (10): 3096-101). In addition, a small deletion in one of the two ITRs allows packaging of self-complementary vectors, in which the genome self-anneals after viral uncoating. This results in more efficient transduction of cells but reduces the coding capacity by half (McCarty, D M et al. Mol Ther. 2008; 16 (10): 1648-56; McCarty, D M et al. Gene Ther. 2001; 8 (16): 1248-54).

In some embodiments, a polynucleotide is delivered to a cell using a transposon/transposase system. For example, the piggyBac™ transposon system may be used. A piggyBac™ transposon is a mobile genetic element that efficiently transposes between vectors and chromosomes via a "cut and paste" mechanism (Woodard et al. 2015). During transposition, the piggyBac™ transposase recognizes transposon-specific inverted terminal repeat sequences (ITRs) located on both ends of the transposon vector and efficiently moves the contents from the original sites and integrates them into TTAA chromosomal sites. The piggyBac™ transposon system facilitates efficient integration of a polynucleotide into a cell genome.

Thus, in some embodiments, the method further comprises delivering to a PSC a transposon comprising an engineered polynucleotide and also delivering a transposase.

In some embodiments, an engineered polynucleotide is delivered to a cell using electroporation. Electroporation is a physical transfection method that uses an electrical pulse to create temporary pores in cell membranes through which the engineered polynucleotide can pass into cells. See, e.g., Chicaybam I. et al. *Front. Bioeng. Biotechnol.,* 23 Jan. 2017.

Following transfection, the engineered polynucleotides may be integrated into the genome of a PSC. In some embodiments, an engineered polynucleotide may further comprise an antibiotic resistance gene to confer resistance to an antibiotic used in an antibiotic drug selection process. In this way, a 'pure' population of cells comprising an integrated engineered polynucleotide may be obtained. In some embodiments, a population of cells comprising an integrated engineered polynucleotide are selected using antibiotic drug selection. Antibiotic drug selection is the process of treating a population of cells with an antibiotic so that only cells that are capable of surviving in the presence of said antibiotic will remain in the population. Non-limiting examples of antibiotics that may be used for antibiotic drug selection include: puromycin, blasticidin, geneticin, hygromycin, mycophenolic acid, zeocin, carbenicillin, kanemycin, ampicillin, and actinomycin.

Culture Media

The methods provided herein, in some embodiments, comprise culturing PSCs in a feeder-free, serum-free culture media. Culture media may comprise, for example, a solubilized basement membrane preparation extracted from the Engelbreth-Holm-Swarm (EHS) mouse sarcoma (e.g., Corning® Matrigel® Matrix) (coated at ~75 μl/cm$^2$ to ~150 μl/cm$^2$ of lot-based diluted suspension). In some embodiments, the solubilized basement membrane preparation comprises one or more extracellular matrix (ECM) protein and one or more growth factor. For example, the ECM proteins may be selected from Laminin, Collagen IV, heparan sulfate proteoglycans, and entactin/nidogen.

In some embodiments, culture media further comprises one or more growth factor, for example, selected from recombinant human basic fibroblast growth factor (rh bFGF) (e.g., 80 ng/ml to 120 ng/ml) and recombinant human transforming growth factor β (rh TGFβ) (e.g., 20 pM to 25 pM). In some embodiments, culture media further comprises rh bFGF and rh TGFβ. In some embodiments, culture media comprises mTeSR™ Plus medium (STEMCELL Technologies).

In some embodiments, a first induction media comprises one or more of (e.g., 2, 3, 4, or more of) the first induction media comprises one or more of L-alanyl-L-glutamine (e.g., 1.8 mM to 2.2 mM), antibiotic (e.g., penicillin and/or streptomycin) (e.g., 45 U/ml to 50 U/ml), Dulbecco's Modified Eagle Medium (DMEM)/F-12 (e.g., 15 mM HEPES, no glutamine), Advanced RPMI (Roswell Park Memorial Institute) 1640 Medium (with non-essential amino acids and sodium pyruvate), a glycogen synthase kinase (GSK) 3 inhibitor (e.g., 3 μM to 10 μM), a protein inhibitor (e.g. noggin, 2 ng/mL to 20 ng/ml) or small molecule inhibitor (e.g., dorsomorphin, e.g., 100 nM to 400 nM) of the BMP signaling pathway, a small molecule ROCK inhibitor (e.g., 9 μM to 11 μM), and an inducing agent (e.g., doxycycline (e.g., 50 ng/ml to 2000 ng/ml)). For example, the first induction media may comprise DK10 medium, CHIR99021, Y-27632 (a small molecule ROCK inhibitor), and doxycycline.

In some embodiments, the second induction media comprises one or more of (e.g., 2, 3, 4, or more of), L-alanyl-L-glutamine, antibiotic (e.g., penicillin and/or streptomycin), Advanced RPMI 1640 Medium (with non-essential amino acids and sodium pyruvate), DMEM/F-12, and an inducing agent (e.g., doxycycline). For example, the second induction media may comprise DK10 medium and doxycycline.

Advanced RPMI 1640 (Thermo Fisher Scientific) is manufactured with glucose, non-essential amino acids, sodium pyruvate (without L-glutamine and HEPES), vitamins, inorganic salts, proteins (e.g., AlbuMAX® II, human transferrin, sand insulin recombinant full chain), and trace elements.

The DK10 medium used herein comprises KO-SR, glutamine, penicillin, streptomycin, and Dulbecco's Modified Eagle Medium (DMEM)/F-12.

The KnockOut™ Serum Replacement (KO-SR) used herein is a serum-free formulation used as a replacement for fetal bovine serum.

GlutaMAX™ Supplement comprises L-alanyl-L-glutamine, which is a dipeptide substitute for L-glutamine.

CHIR99021 is an aminopyrimidine derivative that is an extremely potent glycogen synthase kinase (GSK) 3 inhibitor, inhibiting both GSK3β ($IC_{50}$=6.7 nM) and GSK3α ($IC_{50}$=10 nM). GSK3 is a serine/threonine kinase that is a key inhibitor of the WNT pathway; therefore, CHIR99021 functions as a WNT activator.

Noggin is a protein that binds and inactivates proteins in the BMP family. Dorsomorphin is a small molecule inhibitor of type I BMP receptor serine/threonine kinases. Both these substances are considered inhibitors of the BMP signaling pathway.

Therapeutic Compositions and Method of Use

The present disclosure provides, in some embodiments, therapeutic compositions comprising the granulosa-like cells produced herein. In some embodiments, the compositions further comprise a pharmaceutically-acceptable excipient. The compositions, in some embodiments, are cryopreserved.

Such compositions may be administered to a subject, such as a human subject, using any suitable route of administration. Suitable routes of administration include, for example, parenteral routes such as intravenous, intrathecal, parenchymal, or intraventricular routes. Suitable routes of administration include, for example, parenteral routes such as intravenous, intrathecal, parenchymal, or intraventricular injection.

In some embodiments, a subject is a human subject. Patients suffering from primary ovarian failure or menopause, in which granulosa cell function is compromised may benefit from the use of these cells. Thus, in some embodiments, the subject has been diagnosed with ovarian failure, and the granulosa cells provided herein are used to treat the ovarian failure. In other embodiments, the subject is going through menopause, and the granulosa cells provided herein are used to treat (e.g., alleviate the symptoms associated with) menopause.

Additionally, such compositions may be used to improve the quality and in vitro maturation of oocytes and/or embryos, for example, during an in vitro fertilization (IVF) process and/or during related assisted reproductive technologies (ART) procedures, such as egg freezing. Such administration methods include for example, co-culture of granulosa-like cells with immature and mature oocytes in vitro. In some embodiments, a subject is a human subject. Such subjects will be undergoing oocyte freezing or fertilization through IVF, for example, and may suffer from infertility, age-related oocyte immaturity, polycystic ovarian syndrome (PCOS) and/or ovarian hyperstimulation syndrome (OHSS), which leave many oocytes immature and unusable. Applications of granulosa-like cells in vitro may improve the quality and usability of these oocytes.

The compositions may be administered to a subject in a therapeutically effective amount. The term "therapeutically effective amount" refers to the number of granulosa required to confer therapeutic effect on a subject, either alone or in combination with at least one other active agent. Effective amounts vary, as recognized by those skilled in the art, depending on the route of administration, excipient usage, and co-usage with other active agents. The quantity to be administered depends on the subject to be treated, including, for example, the strength of an individual's immune system or genetic predispositions. Suitable dosage ranges are readily determinable by one skilled in the art and may be on the order of micrograms of the polypeptide of this disclosure. The dosage of the preparations disclosed herein may depend on the route of administration and varies according to the size of the subject.

It is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited in the present application are incorporated by reference for the purposes or subject matter referenced in this disclosure.

Additional Embodiments

The disclosure also relates to the additional embodiments set out in the numbered paragraphs below:

1. A pluripotent stem cell (PSC) comprising: an engineered polynucleotide comprising an open reading frame encoding a protein selected from NR5A1 and a RUNX family protein.
2. The PSC of paragraph 1, wherein the PSC comprises the engineered polynucleotide comprising an open reading frame encoding NR5A1.
3. The PSC of paragraph 1 or 2, wherein the PSC comprises the engineered polynucleotide comprising an open reading frame encoding a RUNX family protein.
4. The PSC of paragraph 3, wherein the RUNX family protein is RUNX1.
5. The PSC of paragraph 3 or 4, wherein the RUNX family protein is RUNX2.
6. The PSC of any one of the preceding paragraphs, wherein the PSC expresses or overexpresses: NR5A1; RUNX1; RUNX2; NR5A1 and RUNX1; NR5A1 and RUNX2; or NR5A1, RUNX1, and RUNX2.
7. The PSC of any one of the preceding paragraphs, wherein PSC further comprises an engineered polynucleotide comprising an open reading frame encoding a TCF21 protein.
8. The PSC of paragraph 7, wherein the PSC expresses or overexpresses TCF21.
9. The PSC of any one of the preceding paragraphs, wherein PSC further comprises an engineered polynucleotide comprising an open reading frame encoding a GATA4 protein.
10. The PSC of paragraph 7, wherein the PSC expresses or overexpresses GATA4.
11. The PSC of any one of the preceding paragraphs, wherein the open reading frame of the engineered polynucleotide is operably linked to a heterologous promoter.
12. The PSC of paragraph 11, wherein the heterologous promoter is an inducible promoter.
13. A pluripotent stem cell (PSC) comprising: a protein selected from NR5A1 and a RUNX family protein, wherein the protein is overexpressed.
14. The PSC of paragraph 15, wherein the PSC expresses or overexpresses: NR5A1; RUNX1; RUNX2; NR5A1 and RUNX1; NR5A1 and RUNX2; or NR5A1, RUNX1, and RUNX2.
15. The PSC of paragraph 14, wherein the PSC further comprises a TCF21 protein.
16. The PSC of paragraph 15, wherein the PSC expresses or overexpresses TCF21.
17. The PSC of paragraph of any one of claims 14-16, wherein the PSC further comprises a GATA4 protein.
18. The PSC of paragraph of any one of claims 14-17, wherein the PSC expresses or overexpresses GATA4.
19. The PSC of any one of the preceding paragraphs, wherein the PSC is a human PSC.
20. The PSC of any one of the preceding paragraphs, wherein the PSC is an induced PSC (iPSC).
21. The PSC of any one of the preceding paragraphs, wherein the PSC comprises 1-20, optionally 8-10, copies of the engineered polynucleotide comprising the open reading frame encoding the protein selected from NR5A1 and a RUNX family protein (e.g., RUNX1 and/or RUNX2).
22. A composition comprising: a population of the PSC of any one of the preceding paragraphs or described elsewhere herein.
23. The composition of paragraph 22, wherein the population comprises at least 10,000/cm$^2$ of the PSC.
24. A method, comprising: culturing, in culture media, a population of pluripotent stem cells (PSCs) to produce an expanded population of PSCs; and expressing in PSCs of the expanded population a protein selected from NR5A1 and a RUNX family protein to produce granulosa-like cells.
25. The method of paragraph 24, wherein the PSCs of the expanded population comprise an engineered polynucleotide comprising an open reading frame encoding NR5A1.
26. The method of paragraph 24 or 25, wherein the PSCs of the expanded population comprise an engineered polynucleotide comprising an open reading frame encoding a RUNX family protein.
27. The method of paragraph 26, wherein the RUNX family protein is RUNX1.
28. The method of paragraph 26 or 27, wherein the RUNX family protein is RUNX2.
29. The method of any one of paragraph 24-28, wherein the PSCs of the expanded population further comprise an engineered polynucleotide comprising an open reading frame encoding a TCF21 protein.
30. The method of any one of paragraph 24-29, wherein the PSCs of the expanded population further comprise an engineered polynucleotide comprising an open reading frame encoding a GATA4 protein.
31. The method of any one of the preceding paragraphs, wherein the open reading frame of the engineered polynucleotide is operably linked to a heterologous promoter.
32. The method of any one of the preceding paragraphs, wherein the heterologous promoter is an inducible promoter.
33. The method of any one of the preceding paragraphs, wherein the population comprises $1\times10^2$-$1\times10^7$ PSCs.
34. The method of any one of the preceding paragraphs, wherein the population of PSCs is cultured for about 4-10 days.
35. The method of paragraph 34, wherein the population of PSCs is cultured for about 6 days.
36. The method of any one of the preceding paragraphs, wherein the granulosa-like cells are AMHR2$^+$, CD82$^+$, FOXL2$^+$, and/or EPCAM$^-$.
37. The method of paragraph 36, wherein the granulosa-like cells are AMHR2$^+$, CD82$^+$, FOXL2$^+$, and EPCAM$^-$.
38. A method comprising:

(a) delivering to pluripotent stem cells (PSCs) an engineered polynucleotide comprising an inducible promoter operably linked to an open reading frame encoding a protein selected from NR5A1 and a RUNX family protein;

(b) culturing the PSCs in feeder-free, serum-free culture media to produce an expanded population of PSCs; and (c) culturing PSCs of the expanded population in a series of induction media comprising an inducing agent to produce AMHR2$^+$, CD82$^+$, FOXL2$^+$, and/or EPCAM$^-$ granulosa-like cells.

39. The method of paragraph 38 comprising delivering to PSCs (i) an engineered polynucleotide comprising an inducible promoter operably linked to an open reading frame encoding NR5A1 and (i) an engineered polynucleotide comprising an inducible promoter operably linked to an open reading frame encoding a RUNX family protein.
40. The method of paragraph 38 or 39, wherein the RUNX family protein is RUNX1.
41. The method of any one of paragraphs 38-40, wherein the RUNX family protein is RUNX2.
42. The method of any one of paragraphs 38-41, wherein the engineered polynucleotide is a transposon and the delivering further comprises delivering a transposase to the PSCs.
43. The method of any one of paragraphs 38-42, wherein the inducible promoter is a chemically-inducible promoter, optionally a doxycycline-inducible promoter.
44. The method of any one of paragraphs 38-43, wherein the feeder-free, serum-free culture media of (b) comprises a solubilized basement membrane preparation extracted from the Engelbreth-Holm-Swarm (EHS) mouse sarcoma.
45. The method of paragraph 44, wherein the solubilized basement membrane preparation comprises extracellular matrix (ECM) proteins and growth factors.
46. The method of paragraph 45, wherein the ECM proteins are selected from Laminin, Collagen IV, heparan sulfate proteoglycans, and entactin/nidogen.
47. The method of any one of paragraphs 38-46, wherein the feeder-free, serum-free culture media of (b) comprises growth factors selected from recombinant human basic fibroblast growth factor (rh bFGF) and recombinant human transforming growth factor β (rh TGFβ).
48. The method of any one of paragraphs 38-47, wherein the culturing of (b) is for about 6-24 hours.
49. The method of any one of paragraphs 38-48, wherein the PSCs of the expanded population of (c) are cultured at a density of about 10,000 cells/cm$^2$ to about 20,000 cells/cm$^2$.
50. The method of any one of paragraphs 38-49, wherein the culturing of (c) comprises culturing the PSCs in a first induction media and culturing the PSCs in a second induction media.
51. The method of paragraph 50, wherein the first induction media comprises one or more of L-alanyl-L-glutamine, antibiotic (e.g., penicillin and/or streptomycin), Dulbecco's Modified Eagle Medium (DMEM)/F-12, Advanced RPMI (Roswell Park Memorial Institute) 1640 Medium, a glycogen synthase kinase (GSK) 3 inhibitor, a small molecule or protein inhibitor of the BMP signaling pathway, a small molecule ROCK inhibitor, and an inducing agent (e.g., doxycycline).
52. The method of paragraph 50 or 51, wherein the culturing the PSCs is a first induction media is for about 36 to about 60 hours, optionally about 48 hours.
53. The method of any one of paragraphs 50-52, wherein the second induction media comprises one or more of L-alanyl-L-glutamine, antibiotic (e.g., penicillin and/or streptomycin), Advanced RPMI 1640 Medium, DMEM/F-12, and an inducing agent (e.g., doxycycline).
54. The method of any one of paragraphs 50-53, wherein the culturing the PSCs in a second induction media is for about 96 to about 144 hours, optionally about 120 hours.
55. The method of paragraph 54, wherein the second induction media is removed and replaced with fresh second induction media at about 24-hour intervals.
56. A granulosa-like cell produced by the method of any one of the preceding paragraphs.
57. An ovarian organoid comprising granulosa-like cells of any one of the preceding paragraphs and human primordial germ cell-like cells (hPGCLCS).
58. The method of any one of the preceding paragraphs further comprising combining the granulosa-like cells with hPGCLCS to form an ovarian organoid.

EXAMPLES

Example 1. Directed Differentiation of hiPSCs to Granulosa-Like Cells by Transcription Factor Expression Ovarian granulosa cells are important for many aspects of female reproduction, including the support of oocyte development and hormonal signaling during the menstrual cycle. Current in vitro models, including primary human or mouse granulosa cells and granulosa cell tumor lines, are inadequate for studying these processes. For example, it was found that the COV434 ovarian tumor line, commonly used as a model for granulosa cells, lacks transcriptional and phenotypic characteristics of bona fide granulosa cells. Previously reported protocols for differentiating iPSCs into granulosa-like cells are either low-yielding or only applicable to mouse cells. To solve this challenge, a robust, scalable method of producing granulosa-like cells by transcription factor (TF)-mediated differentiation of iPSCs was developed.

To begin, a list of candidate TFs to screen for granulosa induction were identified. To generate this list. 22 TFs that were differentially expressed in granulosa cells compared to hESCs and early mesoderm were identified using previously published datasets for these cell types. Five TFs, identified as important in mouse ovarian development by previous developmental biology studies, were also included. Finally, nine additional TFs were identified that were predicted to be upstream of the others on the list, based on a gene regulatory network analysis taking into account co-expression data as well as binding motifs.

Next, a hiPSC line was engineered with a tdTomato reporter for the granulosa-specific protein FOXL2. Additionally, a barcoded cDNA plasmid library was generated for doxycycline-inducible expression of these TFs. By integrating these plasmids into the FOXL2-tdTomato reporter iPSCs, inducing TF expression under various conditions, and capturing barcodes from FOXL2+ cells, a set of TFs that were enriched in the granulosa-like population were determined (FIG. 1).

Based on these results, combinations of TFs of interest were screened in order to see which TFs could best induce a granulosa-like phenotype (FIG. 2). It was found that NR5A1 expression was essential for efficient estradiol production, and that the combination of NR5A1 and a RUNX family member (either RUNX1 or RUNX2) was best for inducing FOXL2 expression and granulosa surface markers. It was further validated that the FOXL2+ granulosa-like cells expressed transcriptional markers of granulosa and gonadal cells, and not markers from the related adrenal lineage (FIG. 3).

Figure 4:
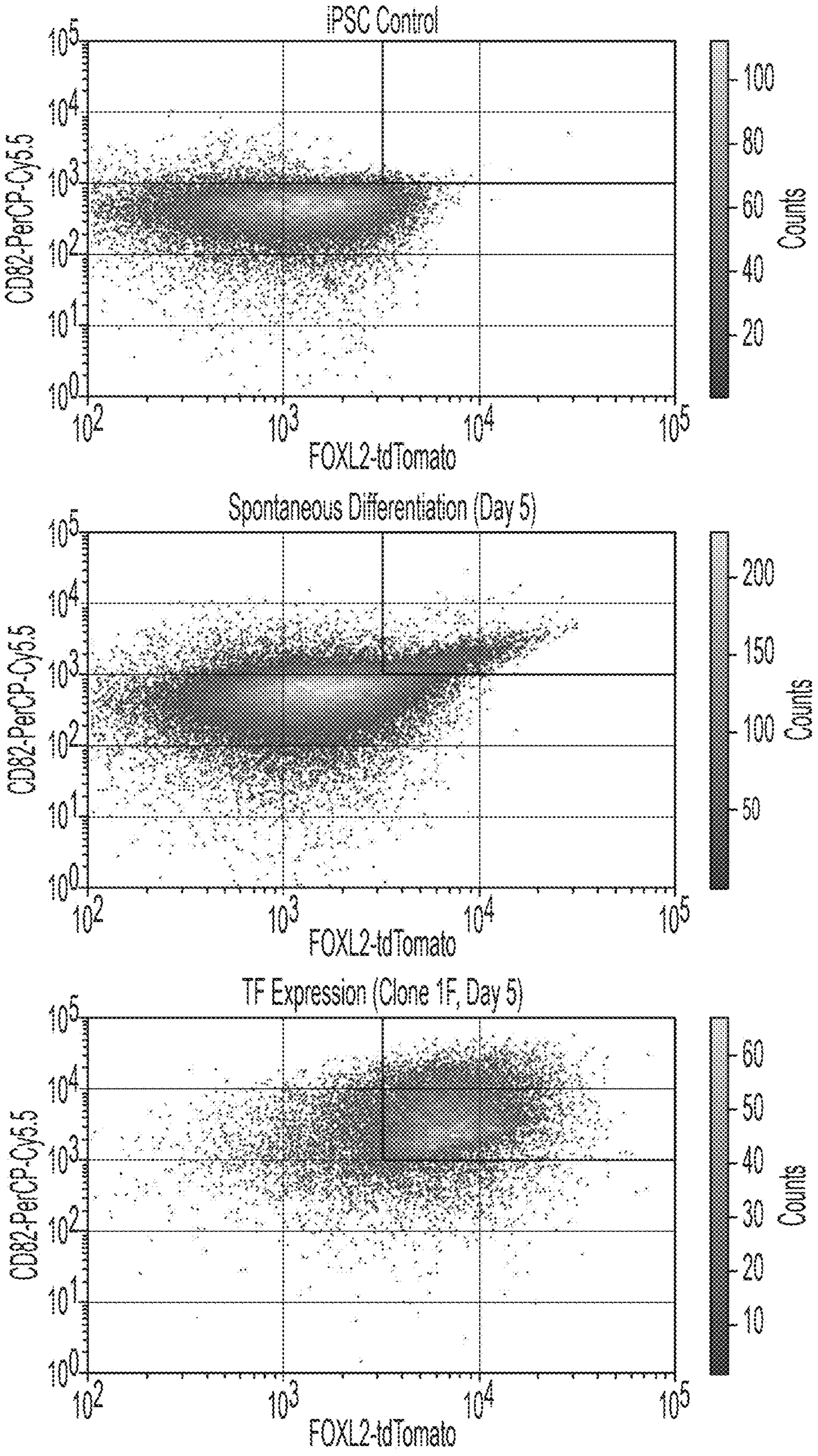
FIG. 4 shows that combination of top TFs generates granulosa-like cells in high yield. Expression plasmids for top TFs (NR5A1, RUNX1, RUNX2, TCF21) were introduced into iPSCs, and single colonies were picked to generate monoclonal lines. Clone 1F has NR5A1, RUNX1, and TCF21 expression plasmids integrated (confirmed by PCR). The 5-day differentiation protocol with doxycycline-induced TF expression resulted in a near-uniform population of FOXL2+CD82+ granulosa-like cells. In comparison, spontaneous differentiation without doxycycline resulted in only a small number of granulosa-like cells.

Next, monoclonal hiPSC lines were generated with the top TFs integrated. After choosing lines with efficient induction of granulosa-like cells (FIG. 4), their hormonal signaling was validated by measuring estradiol production in response to follicle-stimulating hormone (FSH) or forskolin, which increases levels of the second messenger cAMP. It was found that three lines containing integrated expression plasmids for NR5A1, TCF21, and RUNX1 produced estradiol in response to either FSH or forskolin, as expected for granulosa cells (FIG. 5). A fourth line with no RUNX transgene constitutively produced high levels of estradiol, suggesting that RUNX expression is necessary for proper regulation of estradiol production.

Figure 6:
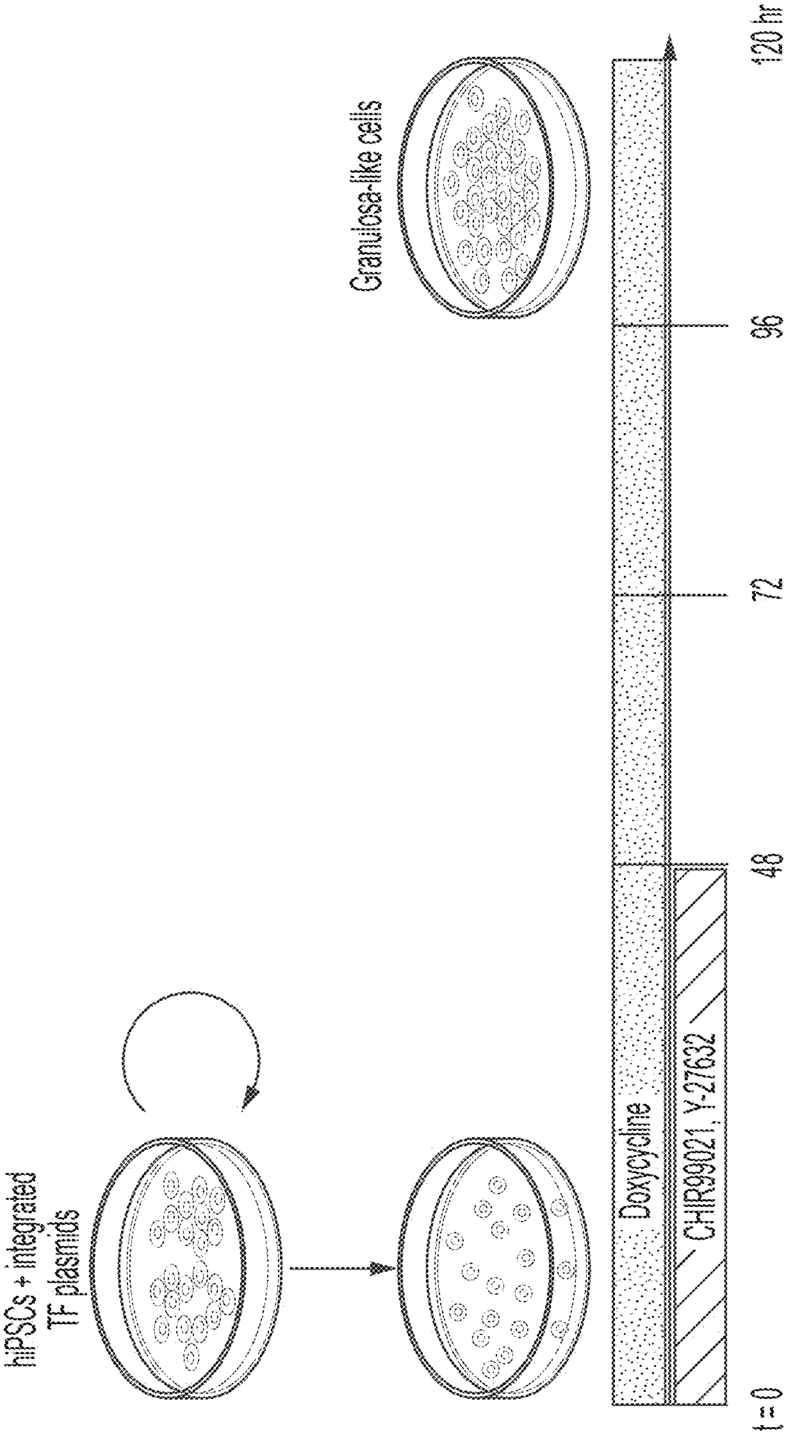
FIG. 6 shows a protocol for inducing granulosa-like cells. hiPSCs containing integrated TF expression plasmids are cultured in mTeSR™ Plus medium on Corning® Matrigel® Matrix. For induction of granulosa-like cells, hiPSCs are dissociated to single cells and plated on Corning® Matrigel® Matrix at a density of 10,000-20,000 per $cm^2$ in DK10 medium (DMEM/F12 with GlutaMAX™ Supplement and 10% Knockout Serum Replacement) plus 3 μM CHIR99021, 10 μM Y-27632, and 1 μg/mL doxycycline to induce TF expression. 48 hours later, and subsequently at 24 hour intervals, the medium is changed and replaced with fresh DK10+1 μg/mL doxycycline. After a total of 120 hours, the granulosa-like cells are ready to use for downstream experiments.

The overall protocol for producing granulosa-like cells is depicted in FIG. 6. hiPSCs containing integrated TF expression plasmids are cultured in mTeSR™ Plus medium on Corning® Matrigel® Matrix. For induction of granulosa-like cells, hiPSCs were dissociated to single cells and plated on Corning® Matrigel® Matrix or Collagen I at a density of ~10,000-20,000 per cm$^2$ in DK10 medium (DMEM/F12 with GlutaMAX™ Supplement and 10% Knockout Serum Replacement) plus ~3-4 μM CHIR99021, ~8-12 μM Y-27632, and ~0.5-3 μg/mL doxycycline to induce TF expression. 48 hours later, and subsequently at 24 hour intervals, the medium was changed and replaced with fresh DK10 medium+~0.5-3 μg/mL doxycycline. After a total of 120 hours, the granulosa-like cells were ready to use for downstream experiments.

In an alternate protocol, iPSCs are cultured on Matrigel or laminin-coated plates and grown to 20-40% confluency in mTeSR Plus medium. For induction of granulosa-like cells, the mTeSR Plus is removed, the iPSCs are washed with phosphate-buffered saline (PBS), and the stage 1 medium, containing Advanced RPMI with GlutaMAX™ Supplement, CHIR99021 (~5-8 μM), and either dorsomorphin (~100-400 nM) or noggin (~4-8 ng/ml), is added. After 48 hours the stage 1 medium is removed and replaced with fresh stage 1 medium. After an additional 48 hours the stage 1 medium is removed and replaced with stage 2 medium, containing Advanced RPMI with GlutaMAX™ Supplement and ~0.5-3 μg/mL doxycycline. The stage 2 medium is changed every 24 hours. Granulosa-like cells can be harvested after a total of ~3-4 days in stage 2 medium (~7-8 days total).

The protocol presented herein has several advantages over previously reported methods. It is rapid, producing granulosa-like cells in ~5-8 days, and the resulting cells are sufficiently pure (FIG. 4) to not require enrichment by FACS. Due to the monolayer format, it is easily scalable (50 million cells were produced at once and the format is compatible with higher throughout assays). Most importantly, the granulosa-like cells transcriptionally (FIG. 3) and phenotypically (FIG. 5) display key characteristics of granulosa cells, making them suitable as a model for ovarian biology.

Example 2. Granulosa-Like Cells Respond to FSH and Perform Steroidogenesis

Figure 5A:
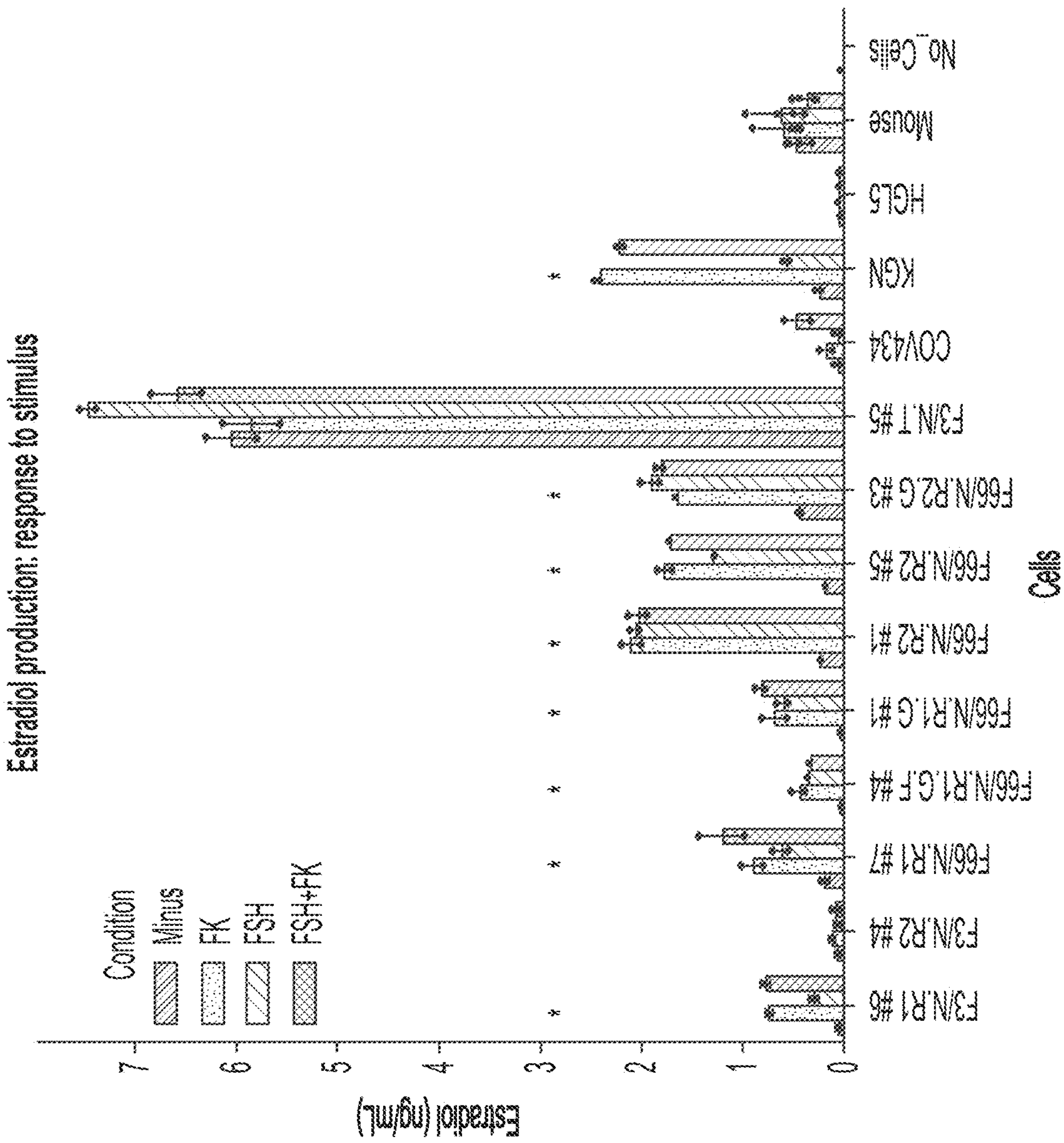
FIGS. 5A-5B show hormonal signaling by granulosa-like cells.
Figure 5B:
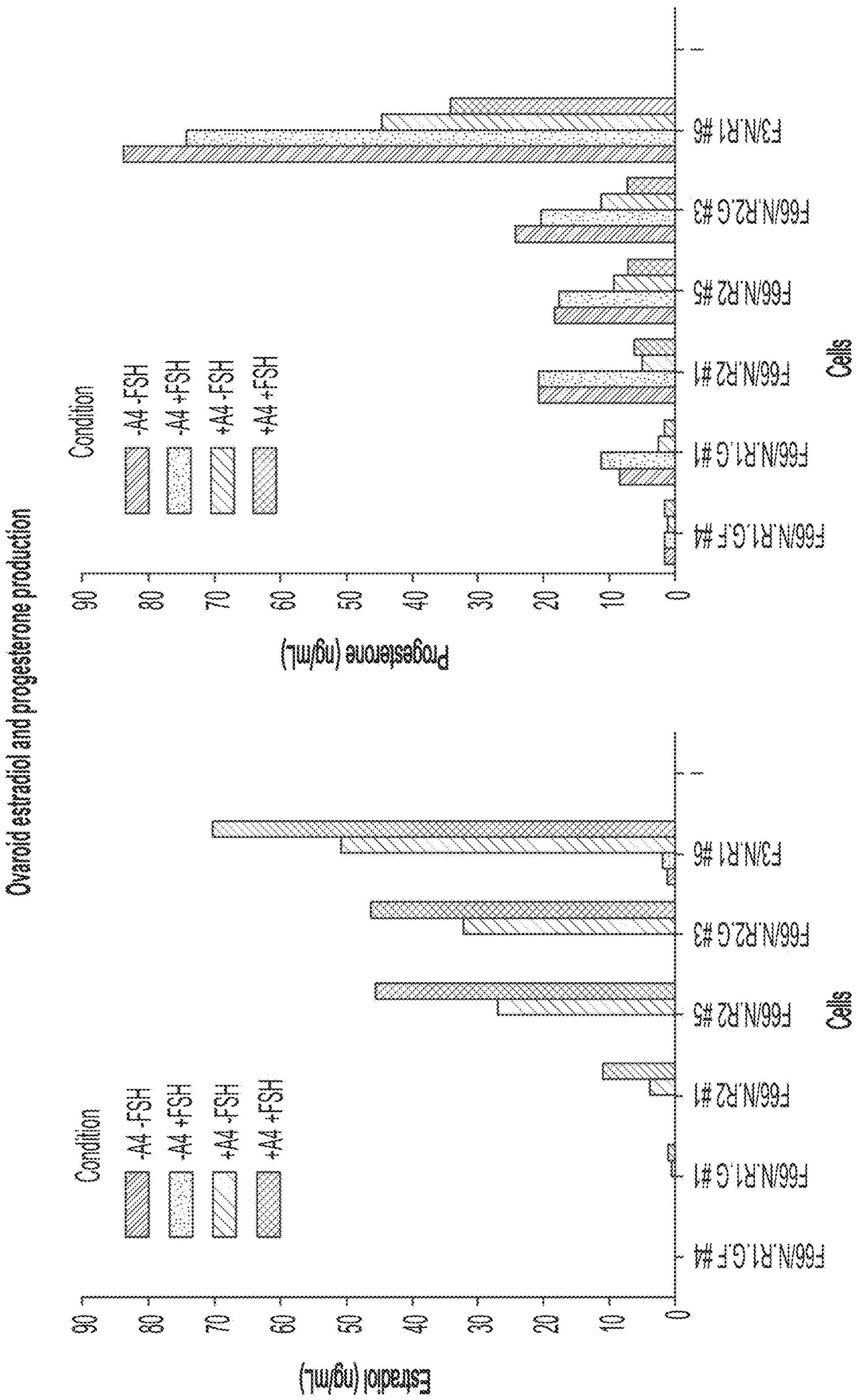

The ability of the granulosa-like cells to carry out one of the key endocrine functions of granulosa cells (i.e., the production of estradiol) was evaluated. In the ovary, theca cells convert cholesterol to androstenedione, which is the substrate for estradiol production in granulosa cells. The rate-limiting step is oxidative decarboxylation by CYP19A1 (aromatase), producing estrone, which is subsequently reduced to estradiol by enzymes in the HSD17B family, typically HSD17B1 in granulosa cells. In vivo, this pathway of estrogen synthesis is stimulated by FSH. The granulosa-like cells were treated with androstenedione, in the presence or absence of FSH or forskolin (which directly increases levels of the FSHR second messenger cAMP). As controls, COV434 and KGN ovarian tumor cells were used, which produce estradiol from androstenedione, as well as immortalized primary human granulosa cells (HGL5) and primary adult mouse ovarian somatic cells. The granulosa-like cells produced estradiol from androstenedione, and in seven out of the nine monoclonal lines tested, this steroidogenic activity significantly increased upon stimulation with FSH or forskolin (FIG. 5A). One of the granulosa lines (F3/N.T #5) produced high levels of estradiol in all conditions, and this line, unlike the others, had neither RUNX1 nor RUNX2 expression vectors integrated (data not shown).

The levels of estradiol produced by three FSH-responsive lines were similar to those produced by KGN human granulosa tumor cells, which also showed responses to FSH and forskolin (FIG. 5A). In contrast, COV434 cells, which showed no FSHR expression in the RNA seq data (FIG. 3), were unresponsive to FSH alone, producing estradiol only in the presence of forskolin. HGL5 immortalized human granulosa cells did not produce estradiol under any condition. Primary adult mouse ovarian somatic cells produced similar amounts of estradiol to the hiPSC-derived granulosa-like cells (FIG. 5A); however, the mouse cells did not show a response to FSH or forskolin, possibly because they were already exposed to FSH in vivo. Whether the granulosa-like cells maintained their steroidogenic activity during ovaroid (ovarian organoid) co-culture with hPGCLCs was also investigated. Hormone levels in ovaroid supernatants in the presence or absence of androstenedione and FSH were measured. In addition to estradiol, progesterone was also measured; granulosa cells produce progesterone in vivo after ovulation and formation of the corpus luteum. Production of both hormones in five out of six samples (FIG. 5B) was observed. Estradiol was produced only in the presence of androstenedione supplementation, and levels increased with FSH treatment. Progesterone was produced in all conditions but was highest in the absence of androstenedione.

Example 3. Granulosa-Like Cells Support Germ Cell Development within Ovaroids

Current methods for inducing and culturing human PGC-like cells (hPGCLCs) produce cells corresponding to immature, premigratory PGCs that lack expression of gonadal PGC markers such as DAZL. During fetal development, PGCs mature through interactions with gonadal somatic cells, with DAZL playing a key role in downregulation of pluripotency factors and commitment to gametogenesis. This process has recently been recreated in vitro using mouse fetal ovarian somatic cells, which allowed the development of hPGCLCs to the oogonia like stage. In vitro-derived human granulosa-like cells could perform a similar role, with the potential for eliminating interspecies developmental mismatches. Therefore, the granulosa-like cells were combined with hPGCLCs to form ovarian organoids, which were termed "ovaroids".

Figure 7:
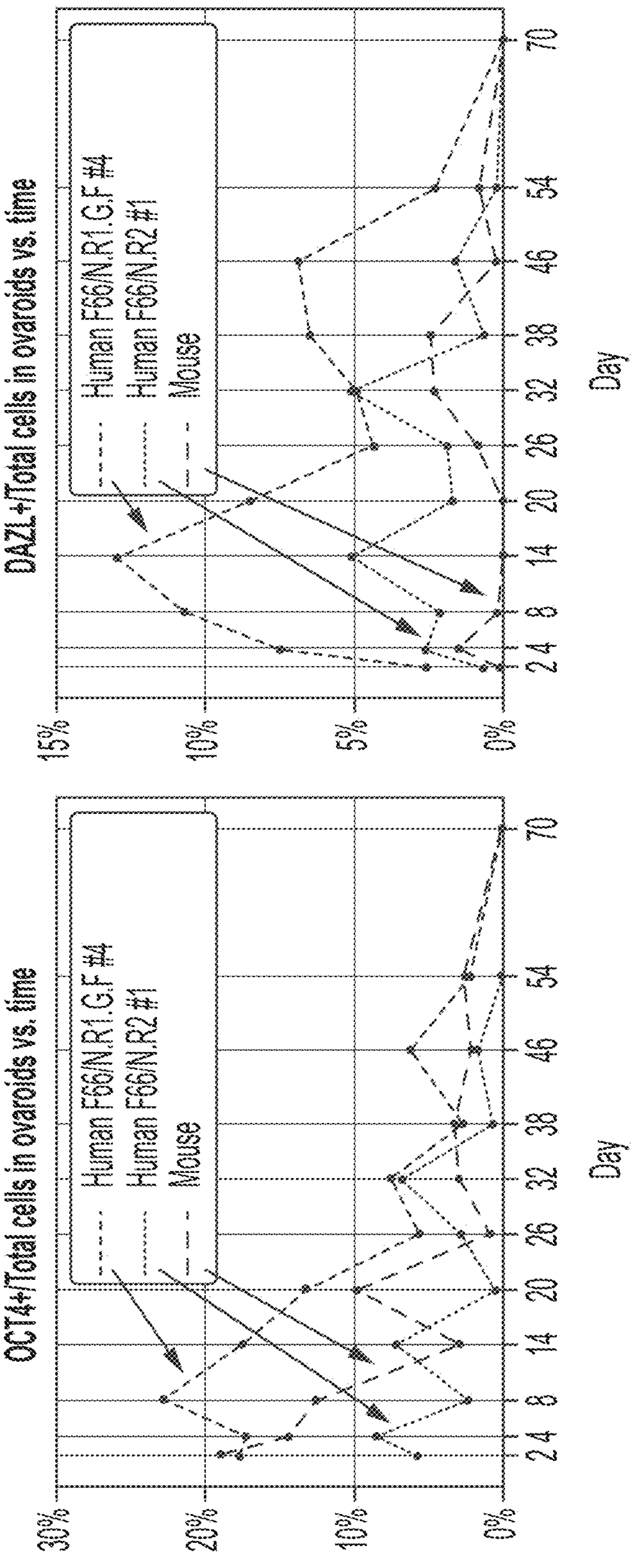
FIG. 7 shows the fraction of $OCT4^+$ and $DAZL^+$ cells relative to the total ($DAPI^+$) over time in human ovaroids and mouse xeno-ovaroids. Counts were performed at eleven time points on images from two replicates of human ovaroids (F66/N.R1.G.F #4 and F66/N.R2 #1 granulosa-like cells+hPGCLCs) and one replicate of mouse xeno-ovaroids.

To generate ovaroids, these two cell types were aggregated in low-binding U-bottom wells, followed by transfer to air-liquid interface Transwell culture. As a comparison, fetal mouse ovarian somatic cells were isolate and aggregate with hPGCLCs. Expression of the mature marker DAZL was observed by immunofluorescence beginning in a subset of OCT4+ hPGCLCs at 4 days of co-culture with hiPSC-derived granulosa-like cells (data not shown). In contrast, robust DAZL expression in co-culture with mouse cells was not observed until day 32 (data not shown), with fainter expression visible at day 26. Similarly, in a previous study using the same hPGCLC line and anti-DAZL antibody, DAZL expression was observed only after 77 days of co-culture with mouse fetal testis somatic cells. The fraction of $DAZL^+$ cells reached its maximum at day 14 in human ovaroids and day 38 in mouse ovaroids (FIG. 7). In human ovaroids, the fraction of $OCT4^+$ cells declined after day 8. In mouse ovaroids, the fraction of $OCT4^+$ cells also declined over time. At day 16 in human ovaroids, $DAZL^+$ $OCT4^-$ cells were also apparent (in situ images not shown) in addition to $DAZL^+$ $OCT4^+$ cells, and past day 38 there were more DAZL+ cells than OCT4+ cells in total (FIG. 7). The downregulation of OCT4 in $DAZL^+$ oogonia occurs in vivo during the $2^{nd}$ trimester of human fetal ovarian development; however, the transition of DAZL to exclusively cytoplasmic localization that was reported to take place at this stage was not observed. Expression of TFAP2C, an early-stage PGC marker, declined during ovaroid culture and was almost entirely absent by day 8. By contrast, SOX17 expression was still visible on day 8, and OCT4 and DAZL expression continued to day 54. Although this system allowed the rapid development of hPGCLCs to the gonadal stage, the number of germ cells in both hiPSC-derived and mouse-derived ovaroids declined over prolonged culture (FIG. 7), indicating that either they were dying or differentiating into other lineages. Unlike mouse-derived ovaroids, the hiPSC-derived ovaroids cultured on Transwells gradually flattened and widened, and by day 38 were largely collapsed.

Figure 8A:
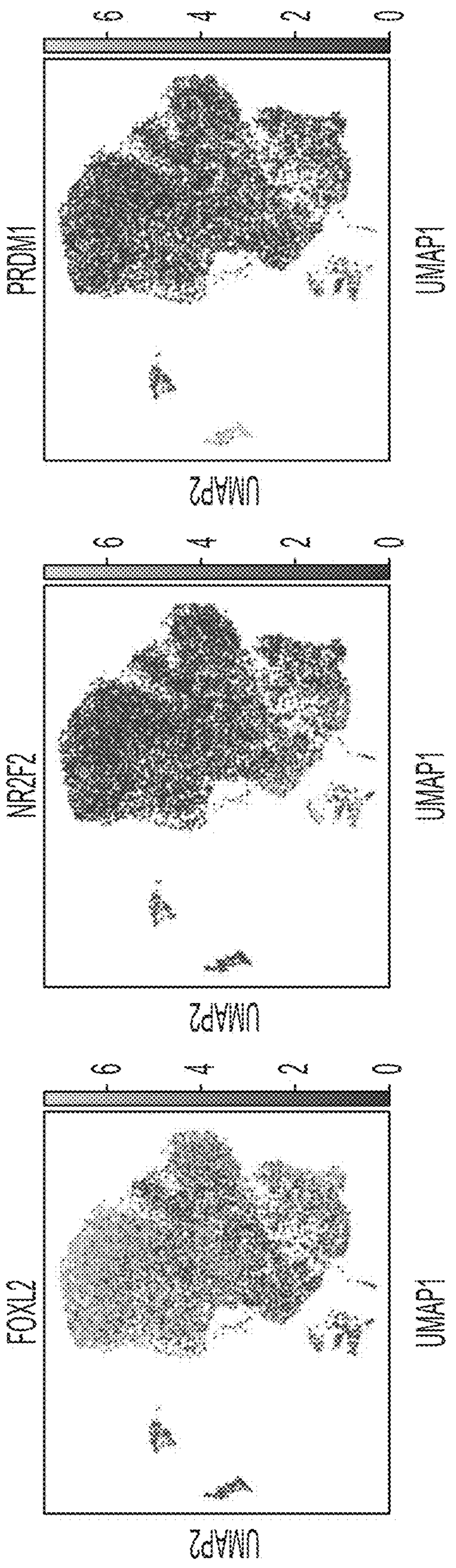
FIGS. 8A-8D show scRNA-seq analysis of ovaroids (F66/N.R1.G.F #4 granulosa-like cells+hPGCLCs). Data from all samples (days 2, 4, 8, and 14) were combined for joint dimensionality reduction and clustering.
Figure 8B:
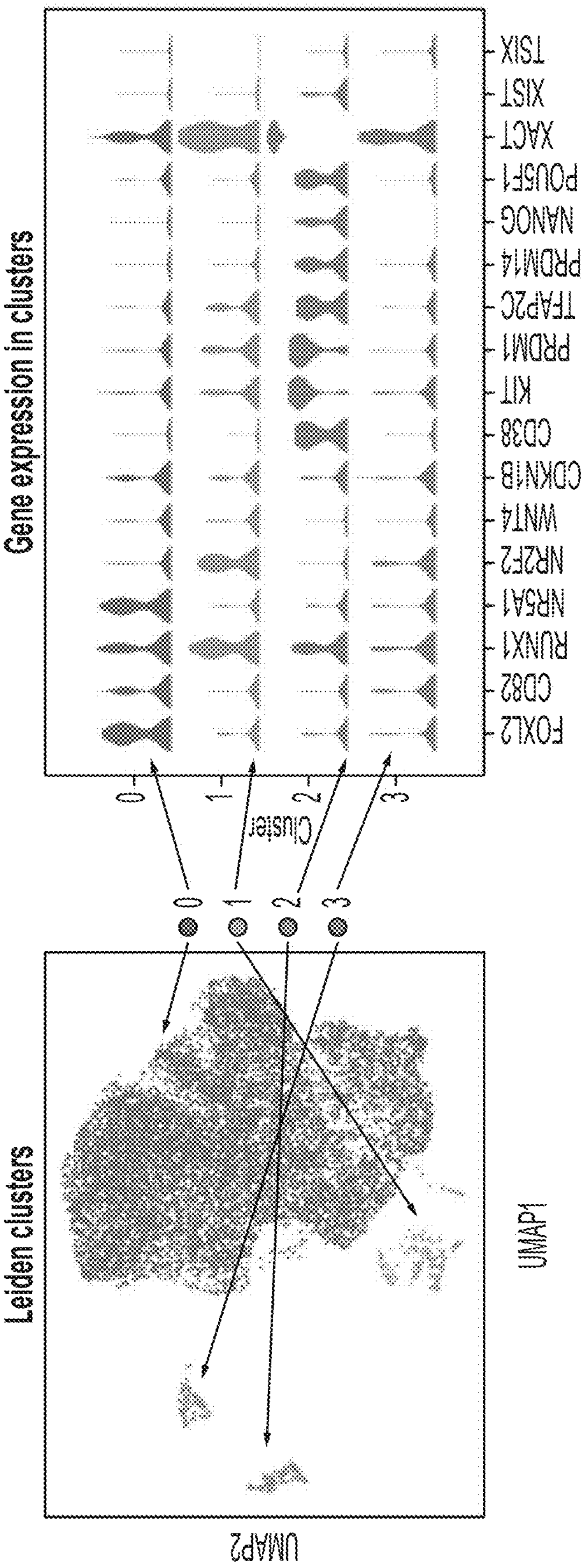

Nonetheless, in these longer-term experiments, the formation of empty follicle-like structures composed of cuboidal AMHR2+ FOXL2+ granulosa-like cells was observed (in situ images not shown), suggesting that the TFs could drive folliculogenesis even in the absence of oocytes. Follicle-like structure formation was first visible at day 16, and at day 26 the largest of these structures had grown to 1-2 mm diameter. At day 70, ovaroids had developed follicles of a variety of sizes, mainly small single-layer follicles but also including antral follicles. Cells outside of the follicles stained positive for NR2F2, a marker of ovarian stromal and theca cells. To further examine the gene expression of hPGCLCs and somatic cells in this system, scRNA-seq was performed on dissociated ovaroids at days 2, 4, 8, and 14 of culture, and clustered cells according to gene expression. As expected, the largest cluster (cluster 0) contained cells expressing granulosa markers such as FOXL2, WNT4, and CD82 (FIGS. 8 and 8B). Cells expressing markers of secondary/antral granulosa cells such as FSHR and CYP19A1 were also found within this cluster, although these were much less numerous. A smaller cluster (cluster 1) expressing the ovarian stromal marker NR2F2 was also present. NR2F2 is expressed by both stromal and theca cells, but the cells in cluster 1 did not express 17α-hydroxylase (CYP17A1), indicating that they could not produce androgens and were not theca cells.

A cluster of hPGCLCs expressing marker genes such as CD38, KIT, PRDM1, TFAP2C, PRDM14, NANOG, and POU5F1 was also observed. Notably, X-chromosomal lncRNAs XIST, TSIX, and XACT were all more highly expressed (an average of ~80-fold, ~20-fold, and ~2900-fold, respectively) in the hPGCLCs relative to other clusters (FIG. 8B), suggesting that the hPGCLCs were starting the process of X-reactivation, which in hPGCs is associated with high expression of both XIST and XACT. The X-chromosomal HPRT1 gene, known to be more highly expressed in cells with two active X chromosome, was also ~3-fold upregulated.

Figure 8C:
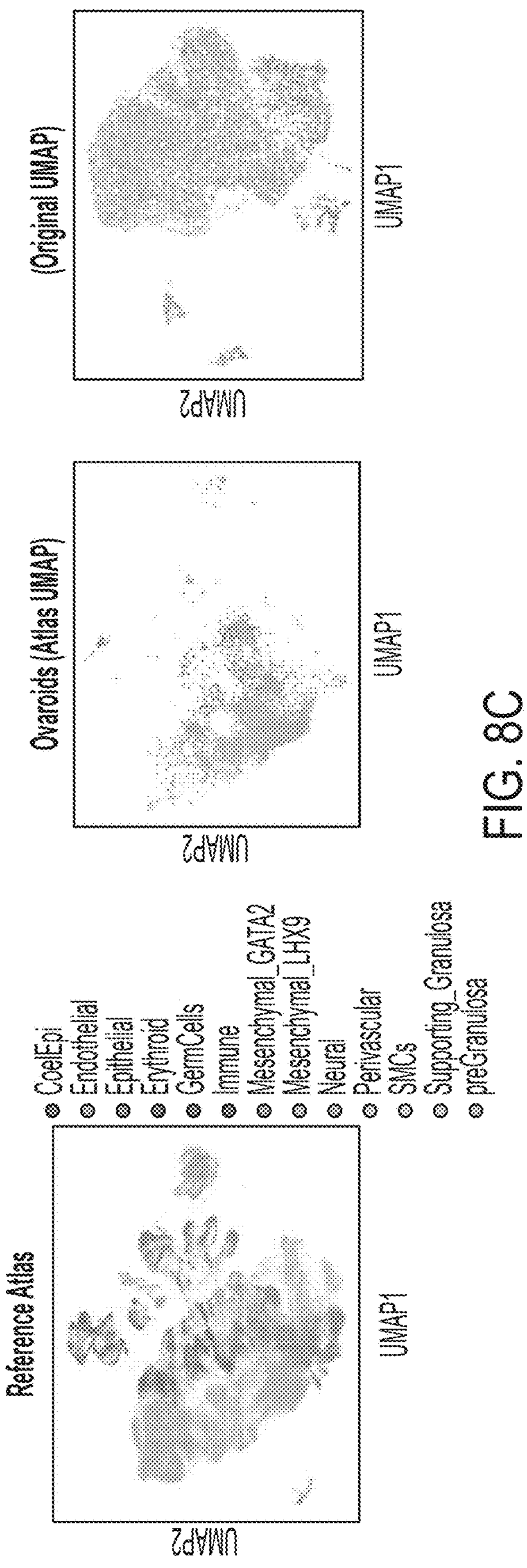

Next, the in vitro-generated ovaroids were compared to a reference atlas of human fetal ovarian development. Scanpy ingest was used to integrate samples into the atlas and annotate each cell with the closest cell type from the in vivo data (FIG. 8C). The ovaroids consisted mainly of granulosa, gonadal mesenchyme, and pre-granulosa lineages (FIG. 8D), with a small fraction of coelomic epithelium. The fraction of granulosa cells increased from day 2 through day 8, potentially representing a maturation of the somatic cell population. As expected, neural, immune, smooth muscle, and erythroid cells, which were present in fetal ovaries, were completely absent from the ovaroids. Epithelial, endothelial, and perivascular cells were detected, but at very low frequency (1% or less), possibly representing a low rate of off-target differentiation.

Figure 8D:
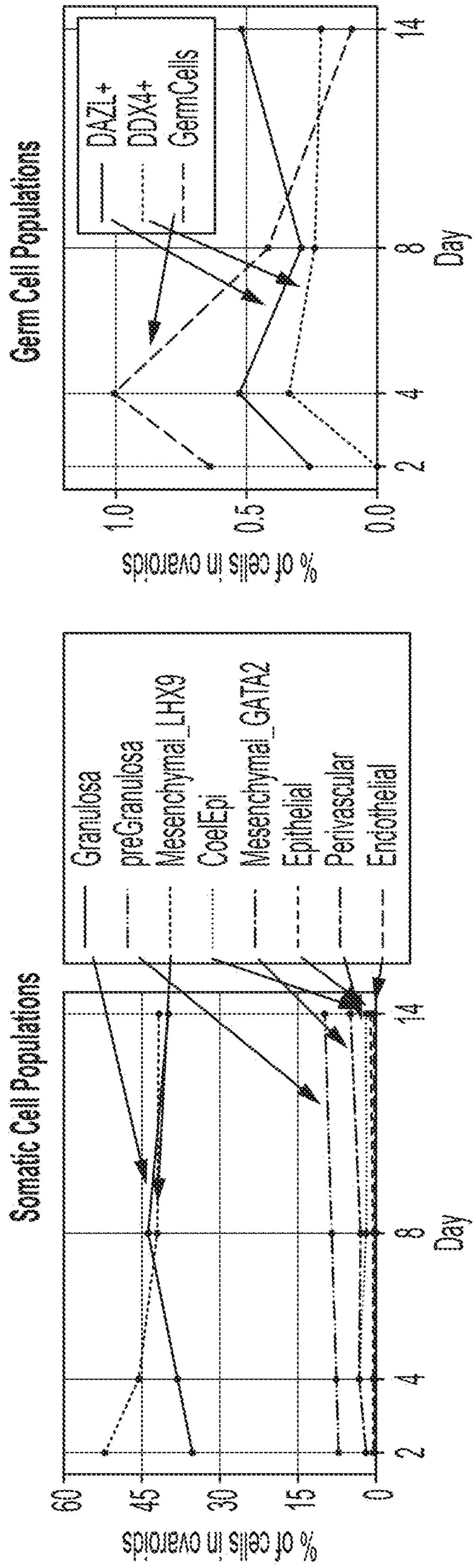

The overall fraction of germ cells was additionally examined, as well as the fraction of cells expressing the gonadal germ cell markers DAZL and DDX4, over the course of the experiment (FIG. 8D). The germ cell population was defined based on the fetal ovary atlas integration. This population increased from days 2 to 4, but declined thereafter. In comparison, the fraction of $DAZL^+$ and $DDX4^+$ cells also increased from days 2 to 4, but remained roughly constant from days 4 to 14 (FIG. 8D). A differential gene expression analysis and gene ontology enrichment were performed on $DAZL^+$ cells relative to DAZL cells. Upregulated genes ($\log_2$ fc>2, n=221) were most highly enriched for terms related to generic developmental 1 processes but also included terms related to adhesion and migration (e.g., "ameboidal-type cell migration"), as well as reproductive system development. Downregulated genes (log 2fc<−2, n=6451) were strongly related to metabolic processes and mitotic cell division. These data suggest that $DAZL^+$ cells in the ovaroids are downregulating their metabolism and proliferation, in agreement with the known role of DAZL in suppressing PGC proliferation.

Methods

Cell Culture

Two parental hiPSC lines were used in this study: ATCC-BXS0116 female hiPSCs, which are referred to as the F3 line, and the F66 line, an in-house hiPSC line derived from the NIA Aging Cell Repository fibroblast line AG07141 using Epi5 footprint-free episomal reprogramming. The karyotypes of parental lines, as well as engineered reporter lines, were verified by Thermo Fisher Cell ID (SNP-based authentication)+Karyostat, and pluripotency was assessed by Thermo Fisher Pluritest. All lines were identified as normal.

hiPSCs were cultured in mTESR Plus medium (Stemcell Technologies) on standard polystyrene plates coated with hESC-qualified Matrigel (Corning). Medium was changed daily. Passaging was performed using 0.5 mM EDTA, or TRYPLE for experiments requiring single-cell dissociation. hiPSCs were treated with 10 μM Y-27632 (Ambeed) for 24 hours after each passage. COV434 cells were cultured in DMEM+10% FBS+1× GlutaMax (Gibco). KGN cells (RIKEN, RCB1154) were cultured in DMEM/F12+10% FBS+1× GlutaMax (Gibco). HGL5 cells (ABM cat. T0650) were cultured in Prigrow IV medium (ABM) with 10% FBS. Passaging was performed with TRYPLE (Gibco). hPGCLCs were cultured in S-CM medium, and passaged with Accutase (Stemcell Technologies). *Mycoplasma* testing was performed by PCR every 3 months; all cells tested negative.

Electroporations

Electroporations were performed using a Lonza Nucleofector with 96-well shuttle, with 200,000 cells in 20 μL of P3 buffer. Pulse setting CA-137 was used for all electroporations. Selection with the appropriate agent was begun 48 hours after electroporation and continued for 5 days. For the agents used in this study, this time was sufficient to give a high-purity final cell population.

Reporter Construction

Homology arms for FOXL2 were amplified by PCR from genomic DNA. A targeting plasmid, containing an in-frame C-terminal T2A-tdTomato reporter, as well as a Rox-PGK-PuroTK-Rox selection cassette (FIG. 2—Figure Supplement 1A), was constructed by Gibson assembly. The plasmid backbone additionally had an MC1-DTA marker to select against random integration. sgRNA oligos targeting the C-terminal region of FOXL2 were cloned into pX330 (Addgene #42230). For generation of the reporter lines, 1 μg donor plasmid and 1 μg sgRNA plasmid were co-electroporated into hiPSCs, which were subsequently plated in one well of a 6-well plate. After selection with puromycin (400 ng/mL), colonies were picked manually with a P20 pipette. The hiPSC lines generated were genotyped by PCR for the presence of wild-type and reporter alleles. Homozygous clones were further verified by PCR amplification of the entire FOXL2 locus (FIG. 2—Figure Supplement 1B) and Sanger sequencing.

To excise the selection cassette, hiPSCs were electroporated with pCAGGS-Dre (1 μg). Selection was performed with ganciclovir (4 μM) and colonies were picked as described above. The excision of the selection cassette was verified by genotyping. Primers used in this study are listed in Supplementary File 1.

TF Plasmid Construction

TF cDNAs were obtained from the TFome39 or the ORFeome76 as Gateway entry clones. These were cloned into a barcoded Dox-inducible expression vector (Addgene #175503) using MegaGate cloning48. The final expression constructs were verified by Sanger sequencing, which also served to determine the barcode sequences for each TF. Two unique barcodes were used per TF during library pooling. Libraries were pooled using an equimolar quantity of each plasmid (measured using QuBit).

TF Screening for Granulosa Differentiation

A pooled library of barcoded TF plasmids was electroporated into FOXL2-tdTomato reporter hiPSCs, typically at 5 fmol library and 500 ng PiggyBac transposase expression plasmid (Systems Bio). These conditions were chosen to give an average copy number of approximately 5/cell (FIG. 2—Figure Supplement 2). Some experiments were also performed at 50 fmol to explore the effects of higher copy numbers. For the screening data presented in FIG. 2, two libraries were used: library #1, containing 35 TFs, and library #2, containing 18 TFs. Library #1 was used only at 5 fmol, whereas library #2 was used at both 5 fmol and 50 fmol.

After selection with puromycin (400 ng/mL), hiPSCs were treated with doxycycline (1 μg/mL) in mTESR Plus medium. In additional experiments, hiPSCs were first differentiated to mesoderm following a previously published protocol77 before doxycycline treatment. In both sets of experiments, doxycycline treatment continued for 5 days, after which the cells were dissociated with TRYPLE and reporter-positive cells were isolated by FACS. Genomic DNA was extracted (QIAamp DNA Micro kit) from reporter-positive and negative cells, as well as from the initial population before doxycycline treatment.

Barcodes were amplified by PCR (KAPA polymerase), using 10 ng input gDNA per reaction and typically 22 PCR cycles (95° C. 15 sec. denature, 58° C. 20 sec. anneal/extend). PCR products were purified using ProNex beads, and a second round of PCR (NEB Q5 polymerase, 6 cycles of 98° C. 5 sec. denature, 61° C. 20 sec. anneal, 72° C. 5 sec. extend, final extension 72° C. 2 min) was performed to add Illumina indices. (Primers are given in Supplementary File 1). These amplicons were again purified using ProNex beads. Samples were normalized and pooled, and barcodes were sequenced on an Illumina MiSeq with 10% PhiX spike-in. To call barcodes, reads were aligned to the set of known barcode sequences. Fold-changes were calculated by comparing barcode frequencies in the sorted FOXL2+ cells to the frequencies in the starting population.

Flow Cytometry/Cell Sorting

Cells were dissociated by treatment with TRYPLE for 5 minutes, which was quenched with 4 volumes of ice-cold DMEM+10% FBS. The suspension was passed through a 70 μm cell strainer. Cells were pelleted (200 g, 5 min) and resuspended in staining buffer (PBS+3% FBS+antibodies, approx. 100 μL per million cells). Staining continued on ice in the dark for 30 minutes. The suspension was diluted with 9 volumes of PBS+3% FBS. Cells were pelleted (200 g, 5 min) and resuspended in PBS+3% FBS+100 ng/mL DAPI. The suspension was kept on ice in the dark until analysis. Flow cytometry was performed on a BD LSRFortessa, and sorting was performed on a Sony SH800 with 100 μm chip.

Antibody capture beads (BD Biosciences, RRID AB_10051478), or hiPSCs expressing tdTomato, were used as compensation controls. Antibodies used are given in the Key Resources table. Data analysis was performed using the Cytoflow Python package (version 1.0.0, github.com/cytoflow/cytoflow)

Protocol for Granulosa Differentiation iPSCs were dissociated with TRYPLE, and plated in DK10 medium (DMEM-F12, 15 mM HEPES, 1× GlutaMax, 10% KSR) with Y-27632 (10 μM), CHIR99021 (3 μM), and doxycycline (1 μg/mL) at a cell density of 12.500/cm$^2$ on Matrigel-coated polystyrene plates. For 24-well plates the medium volume per well was 0.5 mL; for 6-well plates it was 2 mL. 48 hours after plating, the medium was changed to DK10+doxycycline (1 μg/mL), and the medium was subsequently changed every 24 hours. Cells were harvested on day 5 unless otherwise indicated. In the no-TF control differentiation for RNA-seq, the protocol was the same except the cells did not contain TF expression plasmids.

Additional Protocols for Inducing Granulosa-Like Cells hiPSCs containing integrated TF expression plasmids were cultured in mTeSR™ Plus medium on Corning® Matrigel® Matrix. For induction of granulosa-like cells, hiPSCs were dissociated to single cells using TRYPLE and seeded on Corning® Matrigel® Matrix or collagen I coated plates at a density of ~10,000-20,000 per cm$^2$ in DK10 medium (DMEM/F12 with GlutaMAX™ Supplement and 10% Knockout Serum Replacement) plus ~3-5 μM CHIR99021, ~8-12 μM Y-27632, and ~0.5-3 μg/mL doxycycline to induce TF expression. 48 hours later, and subsequently at 24 hour intervals, the medium was changed and replaced with fresh DK10+~0.5-3 μg/mL doxycycline. After a total of ~120 hours, the granulosa-like cells were ready to use for downstream experiments.

hiPSCs containing integrated TF expression plasmids were cultured in mTeSR Plus medium on Matrigel or laminin. When the cultures had reached 20-40% confluency, the medium was removed, the iPSCs were washed with phosphate-buffered saline (PBS), and the stage 1 medium, containing Advanced RPMI with GlutaMAX™ Supplement, CHIR99021 (~6-10 μM), and either dorsomorphin (~100-400 nM) or noggin (~5-8 ng/mL), was added. After 48 hours the stage 1 medium was removed and replaced with fresh stage 1 medium. After an additional 48 hours the stage 1 medium was removed and replaced with stage 2 medium, containing Advanced RPMI with GlutaMAX™ Supplement and ~0.5-3 μg/mL doxycycline. The stage 2 medium was changed every 24 hours. After ~3-4 days in stage 2 medium (~7-8 days total) the granulosa-like cells were ready to use for downstream experiments.

RNA-seq

Total RNA was extracted from sorted FOXL2$^+$ granulosa-like cells using the Arcturus PicoPure kit (Thermo Fisher), or from COV434 cells and hiPSCs using the Monarch Total RNA Miniprep kit (NEB). For experiments involving TF overexpression, TF expression plasmids were integrated into hiPSCs as described above (50 fmol/200,000 cells). After selection with puromycin, TF expression was induced using doxycycline (1000 ng/ml).

Two biological replicates were collected for each sample (iPSC, hiPSC+individual TFs, sorted FOXL2$^+$, no-TF differentiation, KGN, COV434). Libraries were prepared using the NEBNext Ultra II Directional kit following the manufacturer's protocol, and sequenced on an Illumina NextSeq 500 (2×75 bp paired-end reads). The TPM data shown in FIG. 3 were generated using kallisto78 to pseudoalign reads to the reference human transcriptome (Ensembl GRCh38 v96). Differential expression analysis was performed using DESeq2. PantherDB60 was used to calculate gene ontology enrichment for significantly upregulated (log 2fc>3, padj<0.05) and downregulated (log 2fc<−3, padj<0.05) genes for each sample relative to hiPSCs.

TROM Analysis

The Transcriptome Overlap Measure (TROM) method was employed to identify associated genes that capture molecular characteristics of biological samples and subsequently comparing the biological samples by testing the overlap of their associated genes58. TROM scores were calculated as the −log 10 (Bonferroni corrected p value of association) on a scale of 0-300. The TROM magnitude is positively correlated with similarity between two independent samples, with a standard threshold of 12 as a generally-accepted indicator of significant similarity.

Ovaroid Formation with hPGCLC5 and Granulosa-Like Cells

F2 female hPGCLCs (see Key Resources table) were maintained in long-term culture. Briefly, hPGCLCs were cultured on Matrigel in STO-conditioned medium (GMEM with 13% KSR and 1×NEAA, sodium pyruvate, and GlutaMax, all from Gibco), supplemented with SCF (100 ng/ml, Peprotech), ascorbic acid (50 μg/mL, Gibco), and 2-mercaptoethanol (25 μM, Gibco). hPGCLCs were harvested with Accutase. To form ovaroids, granulosa-like cells were harvested with TRYPLE, counted, and mixed with F2 hPGCLCs. For hormone assays in FIG. 3, we used granulosa-like cells from F3/N.R1 #6, F66/N.R1.G.F #4, F66/N.R1.G #7, F66/N.R2 #1, F66/N.R2 #5, and F66/N.R2.G #3. For immunofluorescence experiments in FIGS. 4 and 5, we used F66/N.R1.G.F #4 and F66/N.R2 #1. For scRNA-seq in FIG. 6, we used F66/N.R1.G.F #4.

For each ovaroid, 100,000 granulosa-like cells and 10,000 hPGCLCs were added to each well of a 96-well U-bottom low-bind plate (Corning #7007) in 200 μL of GK15 medium (GMEM, 15% KSR, with 1× GlutaMax, sodium pyruvate, and non-essential amino acids) supplemented with 10 mM Y-27632, 0.1 mM 2-mercaptoethanol, 1 μg/mL doxycycline, 100 ng/mL SCF, and 50 μg/mL primocin. The plate was centrifuged (100 g, 2 min) and incubated (37° C., 5% CO2) for two days. Subsequently, ovaroids were transferred to Transwells (collagen-coated PTFE, 3 μm pore size, 24 mm diameter, Corning #3492) for air-liquid interface culture with aMEM, 10% KSR, 55 μM 2-mercaptoethanol, 500 ng/mL doxycycline, and 50 μg/mL primocin. Typically, 5-6 ovaroids were cultured on each 6-well Transwell. The medium (1.5 mL) was changed every 2 days.

Ovaroid Formation with hPGCLCs and Mouse Fetal Ovarian Somatic Cells

Fetal ovarian somatic cells were isolated from E12.5 female embryos of CD-1 mice (Charles River) as described by Yamashiro et al.65 For each ovaroid, 50,000 fetal ovarian somatic cells and 5,000 F2 hPGCLCs were combined. Ovaroids were cultured as described above. All mouse experiments were approved by the Harvard Medical School Institutional Animal Care and Use Committee (IACUC).

Immunofluorescence

Ovaroids were washed with PBS and fixed with 1% PFA overnight at 4° C. After another PBS wash, ovaroids were detached from the Transwell. In preparation for cryosectioning, ovaroids were transferred to 10% sucrose in PBS. After 24 hr. at 4° C., the 10% sucrose solution was removed and replaced with 20% sucrose in PBS. After an additional 24 hr. at 4° C., the ovaroids were embedded in OCT compound and stored at −80° C. until sectioning.

The ovaroids were sectioned to 10 μm using a Leica CM3050S cryostat. Sections were transferred to Superfrost Plus slides, which were washed with PBS to remove OCT compound. The slides were washed with PBST (0.1% Triton X-100 in PBS) and sections were circled with a Pap pen. Slides were blocked for 30 min. at room temp. with blocking buffer (1% bovine serum albumin and 5% normal donkey serum [Jackson ImmunoResearch, #017-000-121, lot #152961] in PBST). The blocking buffer was removed and replaced with a solution of primary antibodies in blocking buffer, and the slides were incubated overnight at 4° C. The antibody solution was removed and the slides were washed with PBST for 3×5 min. The slides were incubated with secondary antibody and DAPI solution in blocking buffer for 1 hr. at room temp. in the dark, followed by two 5-minute washes with PBST and one wash with PBS. After staining, samples were mounted in Prolong Gold medium and covered with coverslips. Imaging was performed on a Leica SP5 confocal microscope. Antibodies used are given the Key Resources Table. Images were adjusted for brightness (and only for brightness) in ImageJ (version 2.9.0/1.53t), and cell counts for FIG. 4C were performed manually by a researcher who was blinded to the species of the ovaroids.

Single Cell RNA Sequencing

Ovaroids (6 ovaroids per sample, 2 samples per time point) were dissociated using the Miltenyi Embryoid Body Dissociation Kit (Miltenyi #130-096-348). The cells were passed through a 40 μm strainer, fixed using the Parse Biosciences fixation kit, and stored at −80° C. until all time points had been collected. Libraries were prepared using the Parse Biosciences WT Mega v1 kit generating libraries of an average of 450 bp. The ovaroids took up 8 of the 96 samples; the remaining kit capacity was used for other experiments. The libraries were sequenced on an Illumina NovaSeq 2×150 bp S4 flow cell using single index. 6 bp, libraries and a 5% PhiX spike-in. Data were demultiplexed into library fastq files and counts matrices were generated using Parse Bioscience's analysis pipeline (version 0.9.6). Downstream data processing, such as doublet filtering, dimensionality reduction, and clustering, was performed using Scanpy (version 1.8.2) 70. For cell type assignment, the fetal ovarian dataset from the human reproductive cell atlas69 was used as a reference for scanpy ingest.

Collection of Primary Mouse Ovarian Somatic Cells

Female BALB/c mice (age 10-12 weeks) were confirmed to be in proestrus by visual examination. Mice were killed by CO2 exposure followed by cervical dislocation, and ovaries were removed by dissection. Ovaries were placed in HEPES-buffered DMEM/F12 with 0.1% bovine serum albumin (2 ovaries per 1.5 mL tube, with 500 µL medium) and mechanically disrupted by stabbing with forceps. The cell suspensions were strained through a 40 µm strainer to remove oocytes and clumps prior to culture for hormone assays.

Steroid Hormone Assays

Androstenedione (500 ng/mL) was added to the medium on day 4 of granulosa differentiation. FSH (0.25 IU/mL, BioVision #4781-50 lot 5F07L47810) or forskolin (100 µM, Sigma-Aldrich) were also added as indicated. The total medium volume was 0.5 mL per well of 24-well plate. We performed these assays on each of the lines listed in FIG. 3—Source Data 2. For controls using human cell lines (COV434, KGN, or HGL5) or mouse primary ovarian somatic cells, 75,000 cells were seeded per well. After 24 hours, the medium was analyzed for estradiol content by ELISA (DRG International, EIA-2693). Concentrations were calculated with a 4-parameter logistic curve fit using the data from the standards provided in the kit. Samples outside the range of the calibration curve were diluted and re-run.

For measuring hormone production in ovaroids, ovaroids were aggregated as described above. Androstenedione (500 ng/mL) and/or FSH (0.25 IU/mL) were added to the aggregation medium (total volume 200 µL per ovaroid). After 3 days of culture, the medium was removed and analyzed by ELISA for estradiol (DRG International, EIA-2693) and progesterone (DRG International, EIA-1561). Hormone concentrations were calculated as described above.

All references, patents and patent applications disclosed herein are incorporated by reference with respect to the subject matter for which each is cited, which in some cases may encompass the entirety of the document.

The indefinite articles “a” and “an,” as used herein in the specification and in the claims, unless clearly indicated to the contrary, should be understood to mean “at least one.”

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as “comprising,” “including,” “carrying,” “having,” “containing,” “involving,” “holding,” “composed of,” and the like are to be understood to be open-ended, i.e., to mean including but not limited to. Only the transitional phrases “consisting of” and “consisting essentially of” shall be closed or semi-closed transitional phrases, respectively, as set forth in the United States Patent Office Manual of Patent Examining Procedures, Section 2111.03.

The terms “about” and “substantially” preceding a numerical value mean±10% of the recited numerical value.

Where a range of values is provided, each value between and including the upper and lower ends of the range are specifically contemplated and described herein.

What is claimed is:

1. A human induced pluripotent stem cell (hiPSC) comprising:

(i) an exogenous polynucleotide comprising an open reading frame encoding NR5A1 protein; and (ii) an exogenous polynucleotide comprising an open reading frame encoding RUNX2 protein.

2. The hiPSC of claim 1, wherein the hiPSC further comprises an exogenous polynucleotide comprising an open reading frame encoding GATA4 protein.

3. The hiPSC of claim 1, wherein the hiPSC further comprises an exogenous polynucleotide comprising an open reading frame encoding TCF21 protein.

4. The hiPSC of claim 2, wherein the hiPSC further comprises an exogenous polynucleotide comprising an open reading frame encoding TCF21 protein.

5. The hiPSC of claim 1, wherein each of the open reading frames is operably linked to a separate heterologous promoter.

6. The hiPSC of claim 5, wherein each heterologous promoter is independently selected from the group consisting of an alcohol-regulated promoter, a steroid-regulated promoter, a metal-regulated promoter, a pathogenesis-regulated promoter, a temperature-inducible promoter, and a light-responsive promoter.

7. The hiPSC of claim 6, wherein:

(i) the pathogenesis-regulated promoter is a promoter that is inducible by salicylic acid, ethylene, or benzothiadiazole; and/or (ii) the temperature-inducible promoter is a heat shock promoter.

8. The hiPSC of claim 5, wherein each heterologous promoter is independently a tetracycline-inducible promoter or a doxycycline-inducible promoter.

9. The hiPSC of claim 1, wherein the NR5A1 protein has the amino acid sequence of SEQ ID NO: 1 and the RUNX2 protein has the amino acid sequence of SEQ ID NO: 3.

10. The hiPSC of claim 2, wherein the GATA4 protein has the amino acid sequence of SEQ ID NO: 5.

11. The hiPSC of claim 3, wherein the TCF21 protein has the amino acid sequence of SEQ ID NO: 4.

12. The hiPSC of claim 1, wherein each of the polynucleotides is present within a single nucleic acid molecule.

13. The hiPSC of claim 1, wherein each of the polynucleotides is present within separate nucleic acid molecules.

14. A population of hiPSCs, wherein a plurality of the hiPSCs in the population comprises:

(i) an exogenous polynucleotide comprising an open reading frame encoding NR5A1 protein; and (ii) an exogenous polynucleotide comprising an open reading frame encoding RUNX2 protein.

15. The population of hiPSCs of claim 14, wherein the plurality of the hiPSCs in the population further comprises an exogenous polynucleotide comprising an open reading frame encoding GATA4 protein.

16. The population of hiPSCs of claim 14, wherein the plurality of the hiPSCs in the population further comprises an exogenous polynucleotide comprising an open reading frame encoding TCF21 protein.

17. The population of hiPSCs of claim 15, wherein the plurality of the hiPSCs in the population further comprises an exogenous polynucleotide comprising an open reading frame encoding TCF21 protein.

18. The population of hiPSCs of claim 14, wherein each of the open reading frames is operably linked to a heterologous promoter.

19. The population of hiPSCs of claim 18, wherein each heterologous promoter is independently selected from the group consisting of an alcohol-regulated promoter, a steroid-regulated promoter, a metal-regulated promoter, a pathogenesis-regulated promoter, a temperature-inducible promoter, and a light-responsive promoter.

20. The population of hiPSCs of claim 19, wherein:

(i) the pathogenesis-regulated promoter is a promoter that is inducible by salicylic acid, ethylene, or benzothiadiazole; and/or (ii) the temperature-inducible promoter is a heat shock promoter.

21. The population of hiPSCs of claim 18, wherein each heterologous promoter is independently a tetracycline-inducible promoter or a doxycycline-inducible promoter.

22. The population of hiPSCs of claim 14, wherein the NR5A1 protein has the amino acid sequence of SEQ ID NO: 1 and the RUNX2 protein has the amino acid sequence of SEQ ID NO: 3.

23. The population of hiPSCs of claim 22, wherein the plurality of the hiPSCs in the population further comprise an exogenous polynucleotide comprising an open reading frame encoding GATA4 protein, and wherein the GATA4 protein has the amino acid sequence of SEQ ID NO: 5.

24. The population of hiPSCs of claim 23, wherein the plurality of the hiPSCs in the population further comprise an exogenous polynucleotide comprising an open reading frame encoding TCF21 protein, and wherein the TCF21 protein has the amino acid sequence of SEQ ID NO: 4.

25. The population of hiPSCs of claim 14, wherein the plurality of the hiPSCs comprises from $1\times10^2$ to $1\times10^7$ hiPSCs.

* * * * *